United States Patent
Rotello et al.

(10) Patent No.: US 10,786,527 B2
(45) Date of Patent: Sep. 29, 2020

(54) NANOPARTICLE-STABILIZED NANOCAPSULES AND METHODS OF PREPARATION AND USE FOR NUCLEIC ACID DELIVERY

(71) Applicant: University of Massachusetts, Boston, MA (US)

(72) Inventors: Vincent M. Rotello, Amherst, MA (US); Ying Jiang, Sunderland, MA (US); Rui Tang, Amherst, MA (US)

(73) Assignee: University of Massachusetts, Boston, MA (US)

(*) Notice: Subject to any disclaimer, the term of this patent is extended or adjusted under 35 U.S.C. 154(b) by 15 days.

(21) Appl. No.: 15/073,689

(22) Filed: Mar. 18, 2016

(65) Prior Publication Data
US 2017/0119687 A1 May 4, 2017

Related U.S. Application Data

(60) Provisional application No. 62/135,279, filed on Mar. 19, 2015.

(51) Int. Cl.
| | |
|---|---|
| *A61K 9/51* | (2006.01) |
| *A61K 31/713* | (2006.01) |
| *A61K 47/68* | (2017.01) |
| *A61K 47/69* | (2017.01) |

(52) U.S. Cl.
CPC ........ *A61K 31/713* (2013.01); *A61K 47/6875* (2017.08); *A61K 47/6901* (2017.08); *A61K 47/6925* (2017.08); *A61K 47/6929* (2017.08)

(58) Field of Classification Search
None
See application file for complete search history.

(56) References Cited

U.S. PATENT DOCUMENTS

2015/0051265 A1* 2/2015 Gao ................ C12N 15/87
514/44 A

OTHER PUBLICATIONS

Yang et al. (Angew. Chem. Int. Ed., 50, 477-481, 2011 )Drug Delivery Using Nanoparticle-Stabilized Nanocapsules.*
Wexelblatt et al. (J. Org. Chem. 2014, 79, 6766-6774) On Guanidinium . . . .*
Jiang et al. (Angew. Chem. Int. Ed. Engl. 54(2), 506-510, 2015)Direct Cytosolic Delivery of siRNA Using Nanoparticle-Stabilized Nanocapsules.*

* cited by examiner

*Primary Examiner* — Tigabu Kassa
(74) *Attorney, Agent, or Firm* — Milstein Zhang & Wu LLC

(57) ABSTRACT

The invention provides nanoparticle-stabilized nanocapsules, and methods of their preparation and use in delivery of therapeutics, such as nucleic acids. Various embodiments disclosed relate to a nanoparticle-stabilized nanocapsule. Various embodiments disclosed relate to nanoparticle-stabilized nanocapsules for nucleic acid delivery into cells. Various embodiments provide methods of using the nanocapsule for in vivo delivery of the nucleic acid materials.

17 Claims, 17 Drawing Sheets

Specification includes a Sequence Listing.

FIG. 1a) Schematic presentation of cytosolic siRNA delivery

FIG. 1b) Gel retardation assay of NPSC/siRNA

RNase stability of NPSC/siRNA

FIG. 1c) TEM images of NPSC/siRNA

1) NPSC/siRNA
2) siRNA + RNase A 7 mU
3) NPSC/siRNA + RNase A 7 mU
4) siRNA + RNase A 14 mU
5) NPSC/siRNA + RNase A 14 mU
6) siRNA + RNase A 35 mU
7) NPSC/siRNA + RNase A 35 mU RNase stability of NPSC/siRNA 1) 5 pmol siRNA   2) NPSC/siRNA
3) siRNA + RNase A 7 mU
4) NPSC/siRNA + RNase A 7 mU
5) siRNA + RNase A 14 mU
6) NPSC/siRNA + RNase A 14 mU
7) siRNA + RNase A 35 mU
8) NPSC/siRNA + RNase A 35 mU Serum stability of NPSC/siRNA 1) 5 pmol siRNA
2) NPSC/siRNA
3) siRNA + Bovine serum, 1 h
4) NPSC/siRNA + Bovine serum, 1 h
5) siRNA + Bovine serum, 2 h
6) NPSC/siRNA + Bovine serum, 2 h

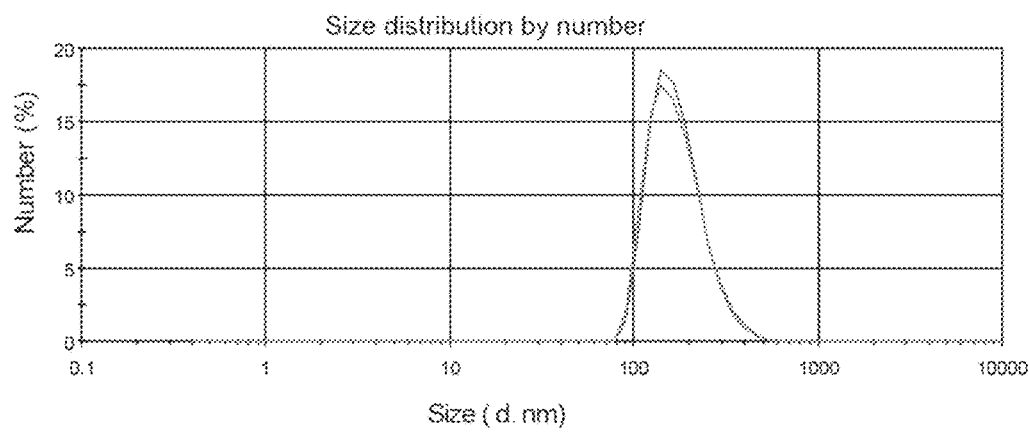
FIG. 5
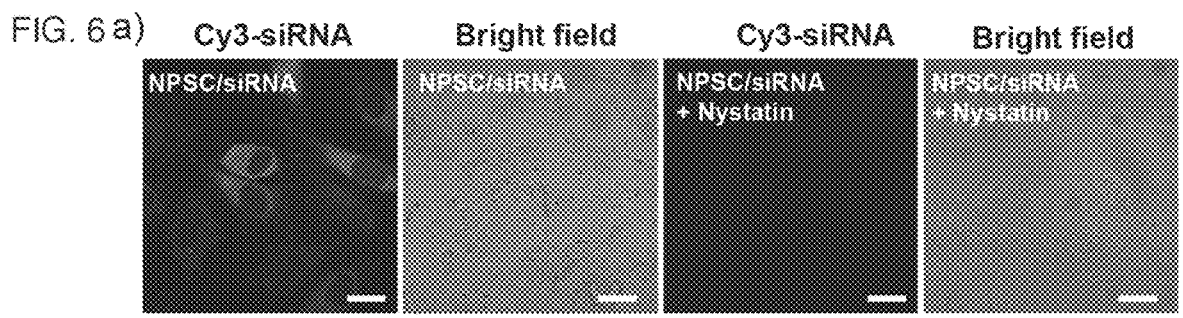
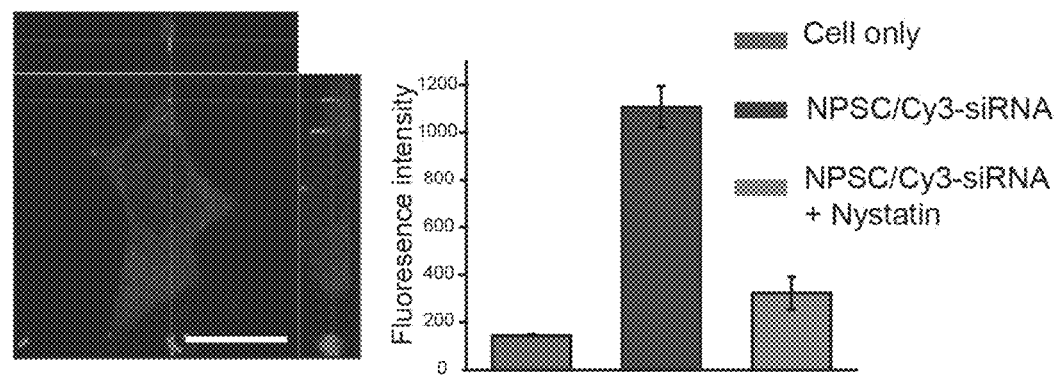
FIG. 6b
FIG. 6c

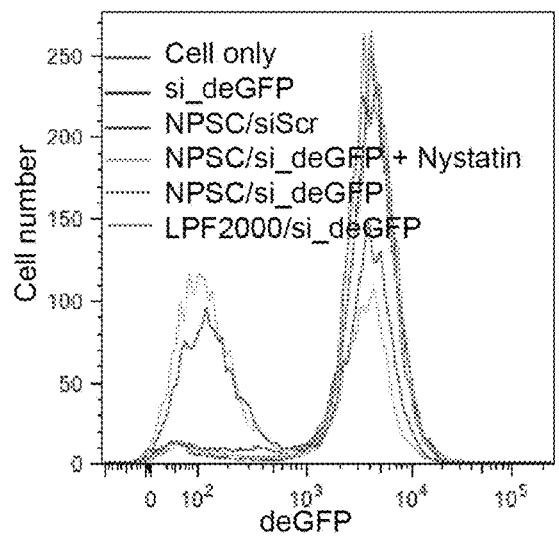 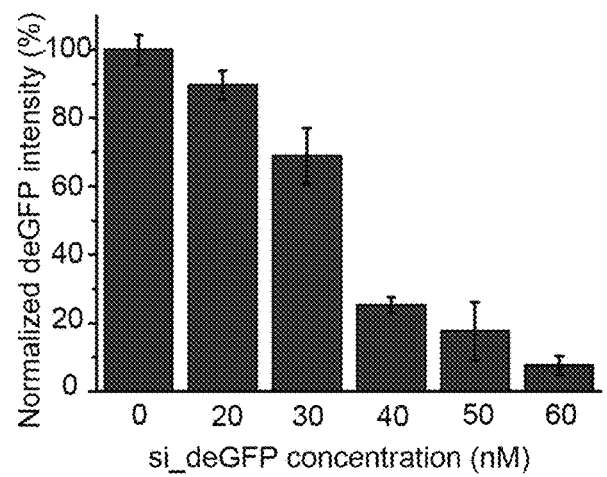
FIG. 9a    FIG. 9b
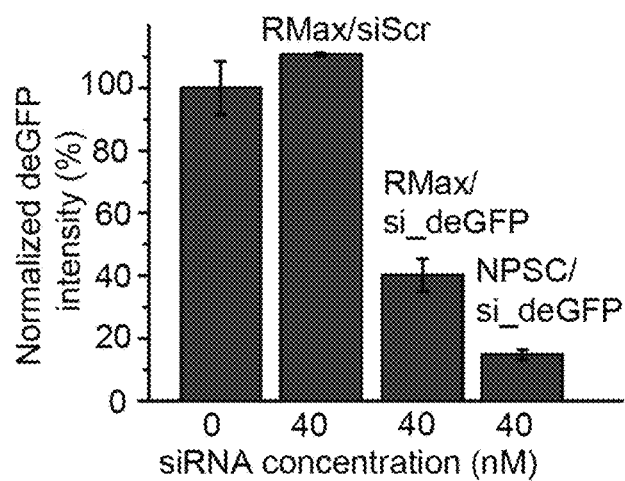
FIG. 10

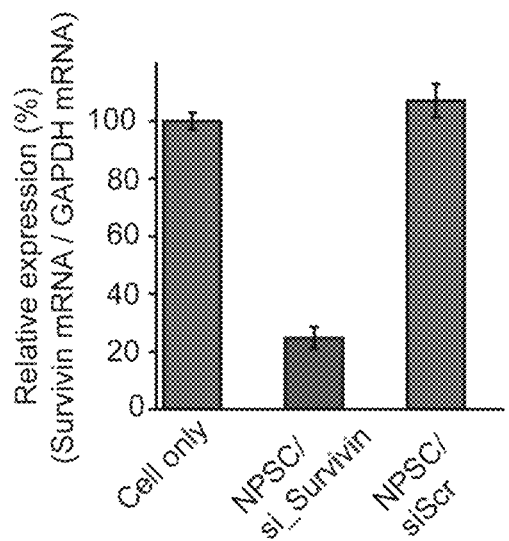
FIG. 22
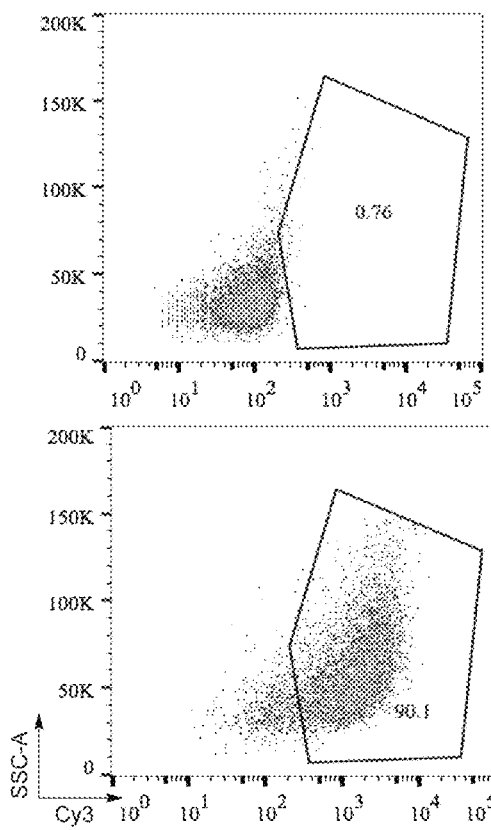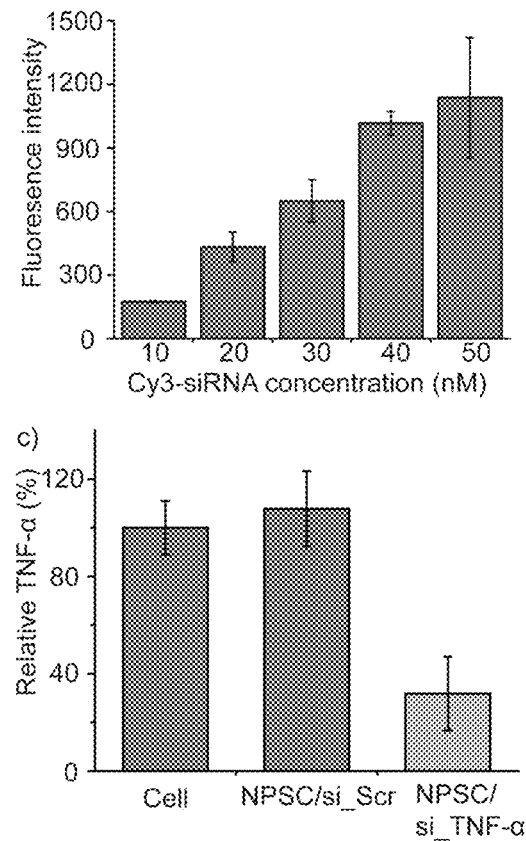
FIG. 23a  FIG. 23b

NANOPARTICLE-STABILIZED NANOCAPSULES AND METHODS OF PREPARATION AND USE FOR NUCLEIC ACID DELIVERY

PRIORITY CLAIMS AND RELATED APPLICATIONS

This application claims the benefit of U.S. Provisional Application No. 62/135,279, filed Mar. 19, 2015, the entire content of which is incorporated herein by reference for all purposes.

Sequence listings and related materials in the ASCII text file named "UOMA043-SEQ_ST25.txt" and created on Nov. 23, 2016 with a size of about 2 kilobytes, is hereby incorporated by reference.

STATEMENT REGARDING FEDERALLY FUNDED RESEARCH OR DEVELOPMENT

This invention was made with government support under Grant Nos. EB0144277 and GM077173 awarded by the National Institutes of Health. The Government has certain rights in the invention.

TECHNICAL FIELDS OF THE INVENTION

The invention generally relates to nanoparticles and applications thereof. More particularly, the invention relates to nanoparticle-stabilized nanocapsules, and methods of their preparation and use in delivery of therapeutics, such as nucleic acids.

BACKGROUND OF THE INVENTION

RNA interference (RNAi) is a biological process in which RNA molecules inhibit gene expression at a post-translational level. The predominant strategy for RNAi uses small interfering RNA to target and cleave complementary mRNA, with concomitant inhibition of protein translation. Since the discovery of RNAi and siRNA, the application of RNAi to knock down the expression of tumor-specific proteins or anti-apoptotic pathways has emerged as a novel therapeutic approach for cancer treatments. (Whitehead, et al. *Nat. Rev. Drug Discov.* 2009, 8, 129-138; Fire, et al. *Nature* 1998, 391, 806-811; Elbashir, et al. *Nature* 2001, 411, 494-498; Pecot, et al. *Nat. Rev. Cancer* 2011, 11, 59-67; Davis, et al. *Nature* 2010, 464, 1067-1070.)

siRNA is a double-strand RNA with a 21-23 base pair length, and hence possesses a high molecular weight and multiple negative charges. These physicochemical characteristics prevent passive diffusion across the membrane of most cell types for RNAi, necessitating vectors for delivery of siRNA into cytosol, where the incorporation of siRNA into RNAi machinery occurs. (Pei, et al. *Nat. Methods* 2006, 3, 670-676; Schroeder, et al. *J. Intern. Med.* 2010, 267, 9-21; Akinc, et al. *Mol. Ther.* 2009, 17, 872-879; Oh, et al. *Adv. Drug Deliver. Rev.* 2009, 61, 850-862; Alabi, et al. *Proc. Natl. Acad. Sci. U.S.A.* 2013, 110, 12881-12886; Petros, et al. *Nat Rev Drug Discov.* 2010, 9, 615-627.)

Recently, nanocarriers have been developed for siRNA delivery, including polymers, liposomes, and inorganic nanoparticles. These siRNA vehicles generally enter cells through endocytic pathways, and are prone to entrapment within subcellular compartments. This entrapment requires increased dosage of siRNA, increasing the possibility of off-target effects. Polyamine polymers and dendrimers can facilitate the escape of siRNA from endosomes by taking advantage of the "proton sponge effect". These highly cationic vehicles are, however, associated with cytotoxicity. (Kwon, *Acc. Chem. Res.* 2012, 45, 1077-1088; Yang, et al. *ACS Nano* 2012, 6, 771-781; Sonawane, et al. *J. Biol. Chem.* 2003, 278, 44826-44831; Yezhelyev, et al. *J. Am. Chem. Soc.* 2008, 130, 9006-9012; Ding, et al. *Mol. Ther.* 2014, 22, 1075-1083; Lv, et al. *J. Control. Release* 2006, 114, 100-109; Vasir, et al. *Adv Drug Deliv Rev.* 2007, 59, 718-28; Lee, et al. *J. Control. Release.* 2008, 125, 25-32; Sahay, et al. *Nature Biotech.* 2013, 31, 653-658; El-Sayed, et al. *AAPS.* 1 2009, 11, 13-22.)

Therefore, effective delivery of siRNA into cytosol remains a key challenge for the application of RNAi, with direct cytosolic delivery providing the desired outcome.

SUMMARY OF THE INVENTION

The invention is based on the unexpected discovery that nanoparticle-stabilized nanocapsules (NPSC) complexed with siRNA provide a highly effective siRNA transfection strategy. Microscopy studies showed that these systems delivered siRNA directly to the cytosol, providing efficient utilization of the siRNA payload by avoiding endosomal sequestration. In addition, it has been demonstrated that such a direct cytosolic siRNA delivery was a temperature-dependent membrane fusion process. Extremely efficient (>90% GFP gene silencing) and effective PLK1 silencing for cancer therapy was achieved with this vehicle, substantially better than commercial available systems. NPSC-siRNA complexes provide effective tools for in vitro applications, particularly in biomedical delivery.

In one aspect, the invention generally relates to a nanoparticle-stabilized nanocapsule The nanocapsule includes: a nanodroplet comprising an amphiphilic fluid; and a plurality of nanoparticles deposed on a surface of the nanodroplet, each nanoparticle comprising a ligand capable of complexing with a nucleic acid material. In certain preferred embodiments, the nanocapsule further includes: one or more nucleic acid materials complexed to at least some of the nanoparticles.

In another aspect, the invention generally relates to a method for delivering a nucleic acid material. The method includes: providing a nanoparticle-stabilized nanocapsule, comprising: a nanodroplet comprising an amphiphilic fluid and a plurality of nanoparticles deposed on a surface of the nanodroplet, wherein a nucleic acid material is complexed to at least some of the nanoparticles; contacting the nanoparticle-stabilized nanocapsule with one or more cells; and allowing the nanoparticle-stabilized nanocapsule to release at least some of the nucleic acid material within the cell.

In yet another aspect, the invention generally relates to a method for delivering a nucleic acid material. The method includes: providing a nanoparticle-stabilized nanocapsule disclosed herein, wherein a nucleic acid material is complexed to at least some of the nanoparticles; contacting the nanoparticle-stabilized nanocapsule with one or more cells; and allowing the nanoparticle-stabilized nanocapsule to release at least some of the nucleic acid material within the cell. In certain embodiments of the method, the nanoparticle-stabilized nanocapsule releases substantially all of the nucleic acid material within the cell.

In yet another aspect, the invention generally relates to a nanoparticle-stabilized nanocapsule, which includes: a nanodroplet comprising a fatty acid; and a plurality of gold nanoparticles on a surface of the nanodroplet, each nanoparticle comprising an amine-containing ligand, wherein at least some of the nanoparticles are complexed with one or more molecules of siRNA, the amine containing ligand having the structure:

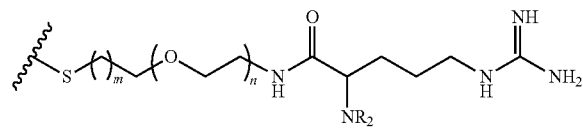

or a salt thereof, wherein m is about 0 to about 1,000 and n is about 0 to about 1,000; wherein the nanoparticle-stabilized nanocapsule has a largest dimension of about 50 nm to about 500 nm, the nanoparticle-stabilized nanocapsule has about 2 to about 100,000 of the nanoparticles, each of the nanoparticles has a largest dimension of about 1 nm to about 200 nm, and each of the nanoparticles has about 1 to about 10,000 of the amine-containing ligands.

In yet another aspect, the invention generally relates to a method of intracellular nucleic acid material delivery. The method includes: contacting a nanoparticle-stabilized nanocapsule with one or more cells, the nanoparticle-stabilized nanocapsule comprising a nanodroplet comprising a fatty acid and a plurality of gold nanoparticles on a surface of the nanodroplet, each nanoparticle comprising an amine-containing ligand, wherein at least some of the nanoparticles are complexed with one or more molecules of siRNA, the amine containing ligand having the structure:

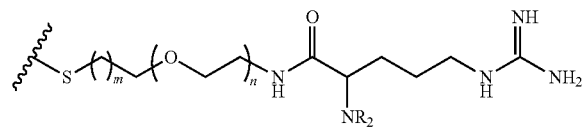

or a salt thereof, wherein m is about 0 to about 1,000 and n is about 0 to about 1,000; wherein the nanoparticle-stabilized nanocapsule has a largest dimension of about 50 nm to about 500 nm, the nanoparticle-stabilized nanocapsule has about 2 to about 100,000 of the nanoparticles, each of the nanoparticles has a largest dimension of about 1 nm to about 200 nm, and each of the nanoparticles has about 1 to about 10,000 of the amine-containing ligands; and delivering at least some of the siRNA into the cell from the nanoparticle-stabilized nanocapsule. In certain embodiments of the method, substantially all of the siRNA from the nanoparticle-stabilized nanocapsule are delivered into the cell.

In yet another aspect, the invention generally relates to a method of forming a nanoparticle-stabilized nanocapsule. The method includes: combining a plurality of nanoparticles comprising an amine-containing ligand with one or more nucleic acid materials to form nanoparticles at least some of which are complexed with the nucleic acid material; and combining the formed nanoparticles with a nanodroplet comprising an amphiphilic fluid to form a nanoparticle-stabilized nanocapsule comprising the nanodroplet comprising the amphiphilic fluid and the formed nanoparticles on a surface of the nanodroplet.

In yet another aspect, the invention generally relates to a method of forming a nanoparticle-stabilized nanocapsule. The method includes: combining a plurality of gold nanoparticles comprising an amine-containing ligand with one or more molecules of siRNA to form nanoparticles at least some of which are complexed with the siRNA, the amine containing ligand having the structure:

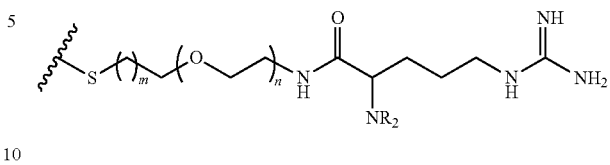

or a salt thereof, wherein m is about 0 to about 1,000 and n is about 0 to about 1,000; and combining the formed nanoparticles with a nanodroplet comprising a fatty acid to form a nanoparticle-stabilized nanocapsule comprising the nanodroplet comprising the fatty acid and the formed nanoparticles on a surface of the nanodroplet. The nanoparticle-stabilized nanocapsule has a largest dimension of about 50 nm to about 500 nm, the nanoparticle-stabilized nanocapsule has about 2 to about 100,000 of the nanoparticles, each of the nanoparticles has a largest dimension of about 1 nm to about 200 nm, and each of the nanoparticles has about 1 to about 10,000 of the amine-containing ligands.

In yet another aspect, the invention generally relates to a kit for forming a nanoparticle-stabilized nanocapsule. The kit includes: an amphiphilic fluid; and a plurality of nanoparticles comprising an amine-containing ligand configured to be combined with one or more nucleic acid materials to form nanoparticles at least some of which are complexed with the nucleic acid material, the formed nanoparticles sufficient for combining with a nanodroplet comprising the amphiphilic fluid to form a nanoparticle-stabilized nanocapsule comprising the nanodroplet comprising the amphiphilic fluid and the formed nanoparticles on a surface of the nanodroplet. In certain embodiments, the kit further includes the nucleic acid materials.

BRIEF DESCRIPTION OF THE FIGURES

FIGS. 1(a)-1(d) illustrate preparation and characterization of NPSC/siRNA: (a) NPSC/siRNA components and schematic presentation of NPSC mediated cytosolic siRNA delivery. (b) Gel electrophoresis study of NPSC/siRNA complexation at molar ratios ranging from $1.1 \times 10^{-4}$ to $11 \times 10^{-4}$. (c) TEM images of NPSC/siRNA. (d) Protection of siRNA from RNase A digestion as evaluated by electrophoresis. 5 pmol of siRNA alone or complexed with NPSC were incubated with 7, 14, and 35 mU RNase A at 37° C. for indicated times.

FIG. 5 illustrates hydrodynamic diameter of NPSC/siRNA complex before (179±9 nm, red line) and after (179±12 nm, green line) nystatin (100 μg/mL) incubation. The nanoparticle sizes were measured by DLS.

FIGS. 6(a)-6(c) illustrate that cholesterol depletion significantly blocks siRNA uptake: (a) CLSM images of HeLa cells treated with Cy3-labeled siRNA (40 nM siRNA complexed with NPSC) without (left) and with (right) a pretreatment of nystatin (100 μg/mL). Scale bars: 20 (b) z-stacked CSLM images of HeLa cells treated with NPSC/Cy3-siRNA complex. The three dimensional cutout at the top of the image shows nanoparticles localize on the cell surface and have not penetrated into the cytosolic portion of the cell. Scale bar: 20 μm. (c) Flow cytometry analysis of Cy3-labeled siRNA uptake in HeLa cells without (blue) or with (green) a pre-treatment of nystatin (100 μg/mL). The error bars represent the standard deviations of three parallel measurements.

FIGS. 9(a)-9(b) illustrate deGFP expression profiles of deGFP-expressing HEK 293 cells with different siRNA treatments: (a) Flow cytometry histograms of deGFP-HEK293 cells treated with NPSC/si_deGFP and controls. 60 nM of si_deGFP or scrambled siRNA was mixed with NPSCs for transfection. (b) Quantitative analysis of deGFP expression in deGFP-HEK293 cells treated with increasing concentrations of NPSC/si_deGFP complexes. The error bars represent the standard deviations of three parallel measurements.

FIG. 10 illustrates deGFP expression profiles of deGFP-expressing HEK 293 cells with different siRNA treatments. RNAi Max (RMax) was used as a positive control to compare the GFP silencing efficiency using NPSC. The normalized deGFP fluorescence intensity was measured by flow cytometry analysis and normalized to cells without treatment. The error bars represent the standard deviations of three parallel measurements.

FIG. 22 illustrates qtPCR of survivin mRNA levels normalized against GAPDH of MCF-7 cells 48 hours after treatment of medium (control), NPSC/siScr (Scr: 40 nM), NPSC/si_Survivin (si_Survivin: 40 nM). The error bars represent the standard deviations of three parallel measurements.

FIGS. 23(a)-23(b) illustrates: (a) Flow cytometry plots of Cy3-siRNA positive RAW 264.7 cells. RAW 264.7 cells without NPSC/Cy3-siRNA (top) and with 40 nM NPSC/Cy3-siRNA (bottom) treatment were harvested for flow cytometry analysis. (b) siRNA dose dependent cellular uptake. c) NPSC/siRNA delivery silenced the TNF-α expression of lipopolysaccharide-stimulated RAW 264.7 macrophages, as shown by ELISA. The error bars represent the standard deviations of three parallel measurements.

DEFINITIONS

Figure 1D:
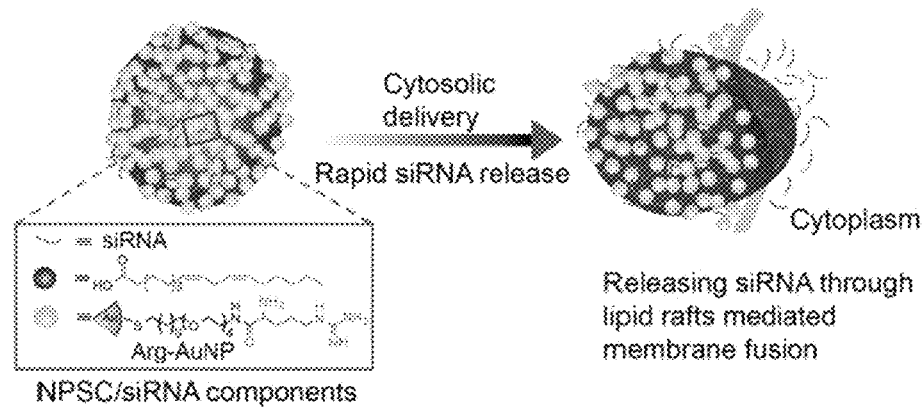
Figure 1D:
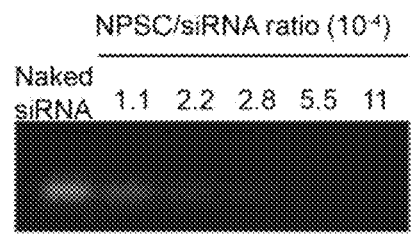
Figure 1D:
Figure 1D:
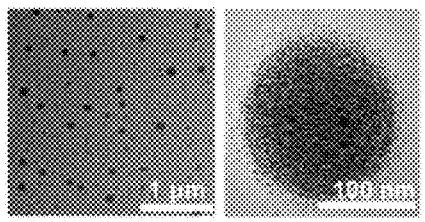

Definitions of specific functional groups and chemical terms are described in more detail below. General principles of organic chemistry, as well as specific functional moieties and reactivity, are described in "Organic Chemistry", Thomas Sorrell, University Science Books, Sausalito: 2006. It will be appreciated that the compounds, as described herein, may be substituted with any number of substituents or functional moieties.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

As used herein, "$C_x$-$C_y$" refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. "$C_1$-$C_{20}$" and the likes similarly encompass the various combinations between 1 and 20 (inclusive) carbon atoms, such as $C_1$-$C_6$, $C_1$-$C_{12}$ and $C_3$-$C_{12}$.

As used herein, the term "alkyl", refers to a hydrocarbyl group, which is a saturated hydrocarbon radical having the number of carbon atoms designated and includes straight, branched chain, cyclic and polycyclic groups. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

As used herein, the term "alkenyl" refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

As used herein, the term "acyl" refers to a group containing a carbonyl group wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

As used herein, the term "aryl" refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

As used herein, the term "heterocyclyl" refers to aromatic and non-aromatic ring compounds containing three or more ring members, of which one or more is a heteroatom such as, but not limited to, N, O, and S.

As used herein, the term "alkoxy" refers to an oxygen atom connected to an alkyl group, including a cycloalkyl group, as are defined herein. Examples of linear alkoxy groupsinclude but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

As used herein, the term "amine" refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

As used herein, the term "amino group" refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

As used herein, the term "antibody" refers to molecules that are capable of binding an epitope or antigenic determinant. The term is meant to include whole antibodies and antigen-binding fragments thereof, including single-chain antibodies. The antibodies can be from any animal origin. Preferably, the antibodies are mammalian, e.g., human, murine, rabbit, goat, guinea pig, camel, horse and the like, or other suitable animals. Antibodies may recognize polypeptide or polynucleotide antigens. The term includes active fragments, including for example, an antigen binding fragment of an immunoglobulin, a variable and/or constant region of a heavy chain, a variable and/or constant region of a light chain, a complementarity determining region (cdr), and a framework region. The terms include polyclonal and monoclonal antibody preparations, as well as preparations including hybrid antibodies, altered antibodies, chimeric antibodies, hybrid antibody molecules, F(ab)$_2$ and F(ab) fragments; Fv molecules (for example, noncovalent heterodimers), dimeric and trimeric antibody fragment constructs; minibodies, humanized antibody molecules, and any functional fragments obtained from such molecules, wherein such fragments retain specific binding.

As used herein, the terms "halo," "halogen," or "halide" group, by themselves or as part of another substituent, mean, unless otherwise stated, a fluorine, chlorine, bromine, or iodine atom.

As used herein, the term "hydrocarbyl" refers to any group comprising only hydrogen and carbon atoms. Hydrocarbyl groups include saturated (e.g., alkyl groups), unsaturated groups (e.g., alkenes and alkynes), aromatic groups (e.g., phenyl and naphthyl) and mixtures thereof. A hydrocarbyl group may be a straight chain, branched, or cyclic hydrocarbon, and can be alkyl, alkenyl, alkynyl, aryl, cycloalkyl, acyl, or any combination thereof. Hydrocarbyl groups can be shown as (C$_a$-C$_b$)hydrocarbyl, wherein a and b are integers and mean having any of a to b number of carbon atoms. For example, (C$_1$-C$_4$)hydrocarbyl means the hydrocarbyl group can be methyl (C$_1$), ethyl (C$_2$), propyl (C$_3$), or butyl (C$_4$). (C$_0$-C$_6$)hydrocarbyl means in certain embodiments there is no hydrocarbyl group.

As used herein, the terms "nucleic acid," "nucleic acid molecule," "oligonucleotide," "polynucleotide," and "nucleotide" are used interchangeably herein to refer to polymeric forms of nucleotides of any length. They can include both double- and single-stranded sequences and include, but are not limited to, cDNA from viral, prokaryotic, and eukaryotic sources; mRNA; genomic DNA sequences from viral (e.g., DNA viruses and retroviruses) or prokaryotic sources; RNAi; cRNA; antisense molecules; ribozymes; siRNA, and synthetic DNA sequences. The term also captures sequences that include any of the known base analogs of DNA and RNA.

As used herein, the term "interfering RNA" or "RNAi" or "interfering RNA sequence" refers to double-stranded RNA (i.e., duplex RNA) that is capable of reducing or inhibiting expression of a target gene (i.e., by mediating the degradation of mRNAs which are complementary to the sequence of the interfering RNA) when the interfering RNA is in the same cell as the target gene. Interfering RNA thus refers to the double-stranded RNA formed by two complementary strands or by a single, self-complementary strand. Interfering RNA may have substantial or complete identity to the target gene or may comprise a region of mismatch (i.e., a mismatch motif). The sequence of the interfering RNA can correspond to the full-length target gene, or a subsequence thereof. Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length).

As used herein, the term "organic group" refers to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based group, and wherein the carbon-based group can be substituted or unsubstituted.

As used herein, the term "room temperature" refers to a temperature of about 15° C. to 28° C.

As used herein, the term "solvent" refers to a liquid that can dissolve a solid, liquid, or gas. Non-limiting examples of solvents are silicones, organic compounds, water, alcohols, ionic liquids, and supercritical fluids.

In various embodiments, salts having a positively charged counterion can include any suitable positively charged counterion. For example, the counterion can be ammonium (NH$_4^+$), or an alkali metal such as sodium (Na$^+$), potassium (K$^+$), or lithium (Li$^+$). In some embodiments, the counterion can have a positive charge greater than +1, which can in some embodiments complex to multiple ionized groups, such as Zn$^{2+}$, Al$^{3+}$, or alkaline earth metals such as Ca$^{2+}$ or Mg$^{2+}$.

In various embodiments, salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

As used herein, the term "substituted" refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O) OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O) R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based group; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000,1" is equivalent to "0.0001." All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

DETAILED DESCRIPTION OF THE INVENTION

The invention provides nanoparticle-stabilized nanocapsules, and methods of their preparation and use in delivery of therapeutics, in particular nucleic acids such as siRNA. As disclosed herein, the NPSC-siRNA based approach provides an effective siRNA transfection strategy and an efficient tool for in vitro biomedical delivery.

Microscopy studies have shown that the delivery systems of the invention transported siRNA directly to the cytosol, providing efficient utilization of the siRNA payload by avoiding endosomal sequestration. In addition, it has been demonstrated that such a direct cytosolic siRNA delivery was a temperature-dependent membrane fusion process. Substantially better than commercial available systems, the NPSC based vehicle enables extremely efficient (>90% GFP gene silencing) and effective PLK1 silencing particularly suited for cancer therapy.

Through still and video microscopy of fluorescently labeled siRNA delivery, direct cytosolic delivery of siRNA using NPSC was confirmed. Electrostatic self-assembly of Arg-AuNP and siRNA on the surface of the "oil" droplet generated stable nanocapsules for siRNA delivery applications. The stability of NPSC relies on the supramolecular guanidine-carboxylate interactions between the arginine-functionalized gold nanoparticles (Arg-AuNP) of the shell and the hydrophobic fatty acid "oil" components in the core (FIG. 1a).

It was demonstrated that this cytosolic siRNA delivery process was mediated by direct fusion between NPSC/siRNA complex and the cell plasma membrane. The cytosolic delivery of siRNA resulted in highly efficient (90%) knockdown of a destabilized green fluorescence protein (deGFP) in deGFP-HEK293 cells. Moreover, the delivery of siRNA targeting polo-like kinase 1(siPLK1) silenced PLK1 expression in cancer cells, resulting in pronounced toxicity. The effective siRNA gene silencing using NPSC indicates the high potency of NPSC-facilitated direct cytosolic siRNA delivery as a platform to knock down targeted genes for disease treatment.

In one aspect, the invention generally relates to a nanoparticle-stabilized nanocapsule The nanocapsule includes: a nanodroplet comprising an amphiphilic fluid; and a plurality of nanoparticles deposed on a surface of the nanodroplet, each nanoparticle comprising a ligand capable of complexing with a nucleic acid material.

In certain preferred embodiments, the nanocapsule further includes: one or more nucleic acid materials complexed to at least some of the nanoparticles.

In certain embodiments of the nanocapsule, the ligand comprises an amino group.

The nanoparticle-stabilized nanocapsule can have any suitable number of nanoparticles on the surface of the nanodroplet. In certain embodiments of the nanocapsule, the nanoparticle-stabilized nanocapsule includes about 2 to about 100,000 (e.g., about 10 to about 100,000, about 100 to about 100,000, about 1,000 to about 100,000, about 10,000 to about 100,000, about 2 to about 50,000, about 2 to about 10,000, about 2 to about 5,000, about 2 to about 1,000, about 2 to about 500, about 2 to about 100, about 2 to about 50, about 2 to about 20) of the nanoparticles. In certain preferred embodiments of the nanocapsule, the nanocapsule includes about 5 to about 5,000 of the nanoparticles.

The nanoparticles in the nanoparticle-stabilized nanocapsule can have any suitable size (e.g., the size including the amine-containing ligands). In certain embodiments of the nanocapsule, each of the plurality of nanoparticles has a largest dimension of about 1 nm to about 200 nm. In certain preferred embodiments of the nanocapsule, each of the plurality of nanoparticles has a largest dimension of about 1 nm to about 200 nm (e.g., about 1 nm to about 100 nm, about 1 nm to about 50 nm, about 1 nm to about 20 nm, about 2 nm to about 200 nm, about 5 nm to about 200 nm, about 10 nm to about 200 nm, about 20 nm to about 200 nm, about 50 nm to about 200 nm, about 100 nm to about 200 nm).

In certain embodiments, the nanoparticles in the nanoparticle-stabilized nanocapsule can have a largest dimension of about 1 nm to about 20 nm, or about 1 nm or less, or about 2 nm, 3, 4, 5, 6, 7, 8, 9, 10, 11, 12, 13, 14, 15, 16, 17, 18, 19, 20, 22, 24, 26, 28, 30, 35, 40, 45, 50, 60, 70, 80, 90, 100, 110, 120, 130, 140, 150, 160, 170, 180, 190, or about 200 nm or more. In various embodiments, the core of the nanoparticles in the nanoparticle-stabilized nanocapsule (e.g., not including the amine-containing ligands) can have a largest dimension of about 1 nm to about 100 nm, or about 1 nm to about 10 nm, or about 1 nm or less, or about 2 nm, 3, 4, 5, 6, 7, 8, 9, 10, 11, 12, 13, 14, 15, 16, 17, 18, 19, 20, 22, 24, 26, 28, 30, 35, 40, 45, 50, 60, 70, 80, 90, or about 100 nm or more.

In certain embodiments, the nanoparticle-stabilized nanocapsule has a largest dimension of about 50 nm to about 1 μm (e.g., about 50 nm to about 1 μm, about 100 nm to about 1 μm, about 200 nm to about 1 μm, about 500 nm to about 1 μm, about 50 nm to about 500 nm, about 50 nm to about 200 nm, about 50 nm to about 100 nm). In certain embodiments, the nanocapsule has a largest dimension of about 100 nm to about 1,000 nm.

In certain embodiments, each of the nanoparticles has about 1 to about 10,000 (e.g., about 2 to about 10,000, about 5 to about 10,000, about 10 to about 10,000, about 50 to about 10,000, about 100 to about 10,000, about 1,000 to about 10,000, about 5,000 to about 10,000, about 1 to about 5,000, about 1 to about 1,000, about 1 to about 500, about 1 to about 100, about 1 to about 50, about 1 to about 20) of the ligand. In certain preferred embodiments, each of the nanoparticles has about 2 to about 2,000 of the ligand.

The nanoparticle can be any suitable nanoparticle. In certain embodiments, the nanoparticle is a quantum dot or a nanoparticle comprising one or more of gold, iron oxide, cobalt ferrite, and silica.

In certain embodiments, the ligand comprises a group selected from guanidine and arginine.

In certain embodiments, the ligand comprises is a terminal arginine group. In certain embodiments, the ligand comprises a $(C_0-C_{20})$hydrocarbyl group comprising a substituted or unsubstituted amino group. In certain embodiments, the ligand is terminated with a $(C_0-C_{20})$hydrocarbyl group comprising a substituted or unsubstituted amine group. In certain embodiments, the $(C_0-C_{20})$hydrocarbyl group is tethered to the nanoparticle via a bond or via a linker that comprises at least one of a substituted or unsubstituted $(C_1-C_{30})$hydrocarbylene interrupted or terminated with 0, 1, 2, or 3 groups independently chosen from —O—, —S—, and substituted or unsubstituted —NH—, and a poly(substituted or unsubstituted $(C_2-C_{10})$hydrocarbyloxy). In certain embodiments, the $(C_0-C_{20})$hydrocarbyl group is tethered to the nanoparticle via a bond or via a linker that comprises at least one of a $(C_1-C_{20})$alkylene and a poly($(C_2-C_3)$alkoxy), wherein the tether is bound to the nanoparticle via an —S—.

In certain embodiments, the ligand has the structure:

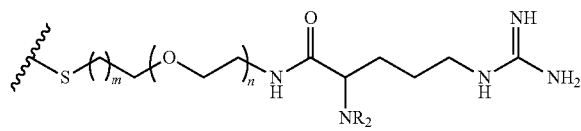

or a salt thereof, wherein each R is independently H or an alkyl group, m is an integer from about 0 to about 1,000, and n is an integer about 0 to about 1,000.

In certain embodiments, each R is H. Each of m and n is independently an integer from about 0 to about 1,000 (e.g., about 0 to about 500, about 0 to about 200, about 0 to about 100, about 0 to about 50, about 0 to about 20, about 0 to about 10, about 0 to about 1,000, about 0 to about 1,000, about 1 to about 1,000, about 2 to about 1,000, about 5 to about 1,000, about 10 to about 1,000, about 20 to about 1,000, about 50 to about 1,000, about 100 to about 1,000, about 1 to about 10, about 1 to about 50, about 10 to about 100, about 10 to about 500).

In certain embodiments, the nanoparticle-stabilized nanocapsule comprises about 1 to about 10,000 (e.g., about 2 to about 10,000, about 5 to about 10,000, about 10 to about 10,000, about 50 to about 10,000, about 100 to about 10,000, about 1,000 to about 10,000, about 5,000 to about 10,000, about 1 to about 5,000, about 1 to about 1,000, about 1 to about 500, about 1 to about 100, about 1 to about 50, about 1 to about 20) molecules of the nucleic acid material. In certain embodiments, the nanoparticle-stabilized nanocapsule has about 2 to about 2,000 molecules of the nucleic acid material.

The nanoparticle-stabilized nanocapsule can include one kind of nucleic acid material, or more than one kind of nucleic acid material (e.g., more than one different kind of siRNA).

The nucleic acid material can have any suitable size. In certain embodiments, in solution the nucleic acid material has a largest dimension of about 0.5 nm to about 100 nm. In certain embodiments, in solution the nucleic acid material can have a largest dimension of about 0.5 nm to about 50 nm, or about 1 nm to about 50 nm, or about 1 nm to about 20 nm, or about 1 nm to about 10 nm, or about 0.5 nm or less, or about 1 nm, 2, 3, 4, 5, 6, 8, 10, 12, 14, 16, 18, 20, 25, 30, 35, 40, 45, 50, 55, 60, 65, 70, 75, 80, 85, 90, 95, or about 100 nm or more.

The nucleic acid material can coordinate to the amine-group in the amine-containing ligand. For example, an acidic proton from a carboxylic acid group can protonate a guanidine group in the amine-containing ligand to form an ammonium ion, which can complex with the carboxylate ion formed from the carboxylic acid group. In other embodiments, a hydroxy group on the nucleic acid can coordinate with a guanidine group in the amine-containing ligand via dipole-dipole interaction.

In certain embodiments, at least one end of the nucleic acid material comprises an —OH group or a —COOH group.

In certain embodiments, the nucleic acid material is selected from DNA and RNA.

In certain embodiments, the nucleic acid material is selected from mRNA (messenger RNA), rRNA (ribosomal RNA), 7SL RNA or SRP RNA (signal recognition particle RNA), tRNA (transfer RNA), tmRNA (transfer-messenger RNA), snRNA (small nuclear RNA), snoRNA (small nucleolar RNA), SmY (SmY RNA), scaRNA (small Cajal body-specific RNA), gRNA (guide RNA), RNase P (ribonuclease P), RNase MRP (ribonuclease MRP), Y RNA, TERC (telomerase RNA component), SL RNA (spliced leader RNA), aRNA or asRNA (antisense RNA), cis-NAT (cis-natural antisense transcript), crRNA (CRISPR RNA), lncRNA (long noncoding RNA), miRNA (microRNA), piRNA (piwi-interacting RNA), siRNA (small interfering RNA), tasiRNA (trans-acting siRNA), rasiRNA (repeat associated siRNA), and 7SK (7SK RNA).

In certain embodiments, the nucleic acid material is siRNA (small interfering RNA).

In certain embodiments, the nanodroplet has a largest dimension of about 50 nm to about 1 μm (e.g., about 100 nm to about 1 μm, about 200 nm to about 1 μm, about 500 nm to about 1 μm, about 50 nm to about 500 nm, about 50 nm to about 200 nm, about 50 nm to about 100 nm). In certain embodiments, the nanodroplet has a largest dimension of about 100 nm to about 1,000 nm.

In certain embodiments, the amphiphilic fluid is about 50 wt % to about 100 wt % (e.g., about 50 wt % to about 100 wt %, about 60 wt % to about 100 wt %, about 70 wt % to about 100 wt %, about 80 wt % to about 100 wt %, about 90 wt % to about 100 wt %) of the nanodroplet. In certain embodiments, the amphiphilic fluid is about 100 wt % of the nanodroplet.

In certain embodiments, the amphiphilic fluid comprises an amphiphilic compound comprising a hydrophobic end and a hydrophilic end.

In certain embodiments, the amphiphilic fluid is at least one of a fatty acid, a glycerolipid, a glycerophospholipid, a sphingolipid, a sterol lipid, a prenol lipd, a saccharaolipid, and a polyketide.

In certain embodiments, the amphiphilic fluid comprises a fatty acid. In certain embodiments, the fatty acid is a $(C_5-C_{50})$ fatty acid. In certain embodiments, the fatty acid is a $(C_{10}-C_{30})$ fatty acid. In certain embodiments, the amphiphilic compound comprises $(C_5-C_{50})$hydrocarbyl-COOH, wherein the $(C_5-C_{50})$hydrocarbyl is substituted or unsubstituted. In certain embodiments, the amphiphilic compound comprises $(C_5-C_{50})$hydrocarbyl-COOH, wherein the $(C_5-C_{50})$hydrocarbyl is unsubstituted.

In certain embodiments, the amphiphilic compound has the structure:

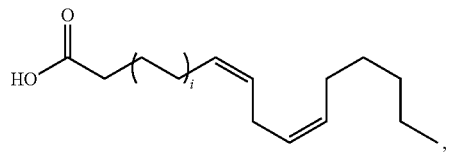

wherein i is an integer from about 1 to about 100 (e.g., about 1 to about 50, about 1 to about 30, about 1 to about 20, about 1 to about 10, about 1 to about 5, about 2 to about 100, about 5 to about 100, about 10 to about 100, about 2 to about 10, about 5 to about 20). In certain embodiments, i is 3, 4, 5, 6, 7, 8, 9, or 10.

In certain embodiments, at least some of the nanoparticles are complexed with an antibody. In certain embodiments, the antibody comprises a tag comprising a carboxylic acid group. In certain embodiments, the antibody comprises a tag comprising a poly(amino acid) group. In certain embodiments, the antibody comprises a tag comprising a glutamic acid group. In certain embodiments, the antibody comprises a tag comprising a poly(glutamic acid) group.

In certain embodiments, the antibody comprises a tag having the structure:

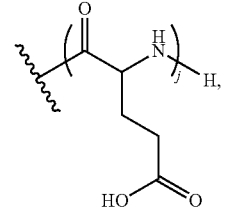

or a salt thereof, or

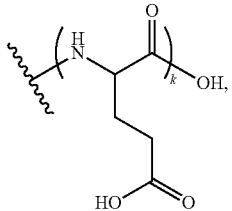

or a salt thereof,
wherein each of j and k is independently an integer about 1 to about 10,000 (e.g., about 2 to about 10,000, about 5 to about 10,000, about 10 to about 10,000, about 50 to about 10,000, about 100 to about 10,000, about 1,000 to about 10,000, about 5,000 to about 10,000, about 1 to about 5,000, about 1 to about 1,000, about 1 to about 500, about 1 to about 100, about 1 to about 50, about 1 to about 20). In certain embodiments, each of j and k is independently an integer about 2 to about 100.

In another aspect, the invention generally relates to a method for delivering a nucleic acid material. The method includes: providing a nanoparticle-stabilized nanocapsule, comprising: a nanodroplet comprising an amphiphilic fluid and a plurality of nanoparticles deposed on a surface of the nanodroplet, wherein a nucleic acid material is complexed to at least some of the nanoparticles; contacting the nanoparticle-stabilized nanocapsule with one or more cells; and allowing the nanoparticle-stabilized nanocapsule to release at least some of the nucleic acid material within the cell.

In certain embodiments of the method, the nanoparticle-stabilized nanocapsule releases at least some of the nucleic acid material within the cytoplasm of the cell. In certain embodiments of the method, the nanoparticle-stabilized nanocapsule releases substantially all of the nucleic acid material within the cytoplasm of the cell.

In yet another aspect, the invention generally relates to a method for delivering a nucleic acid material. The method includes: providing a nanoparticle-stabilized nanocapsule according to any of claims 1-45, wherein a nucleic acid material is complexed to at least some of the nanoparticles; contacting the nanoparticle-stabilized nanocapsule with one or more cells; and allowing the nanoparticle-stabilized nanocapsule to release at least some of the nucleic acid material within the cell.

In certain embodiments of the method, the nanoparticle-stabilized nanocapsule releases substantially all of the nucleic acid material within the cell.

In yet another aspect, the invention generally relates to a nanoparticle-stabilized nanocapsule, which includes: a nanodroplet comprising a fatty acid; and a plurality of gold nanoparticles on a surface of the nanodroplet, each nanoparticle comprising an amine-containing ligand, wherein at least some of the nanoparticles are complexed with one or more molecules of siRNA, the amine containing ligand having the structure:

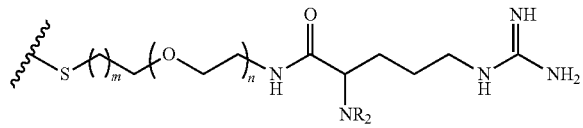

or a salt thereof, wherein m is about 0 to about 1,000 and n is about 0 to about 1,000; wherein the nanoparticle-stabilized nanocapsule has a largest dimension of about 50 nm to about 500 nm, the nanoparticle-stabilized nanocapsule has about 2 to about 100,000 of the nanoparticles, each of the nanoparticles has a largest dimension of about 1 nm to about 200 nm, and each of the nanoparticles has about 1 to about 10,000 of the amine-containing ligands.

In yet another aspect, the invention generally relates to a method of intracellular nucleic acid material delivery. The method includes: contacting a nanoparticle-stabilized nanocapsule with one or more cells, the nanoparticle-stabilized nanocapsule comprising a nanodroplet comprising a fatty acid and a plurality of gold nanoparticles on a surface of the nanodroplet, each nanoparticle comprising an amine-containing ligand, wherein at least some of the nanoparticles are complexed with one or more molecules of siRNA, the amine containing ligand having the structure:

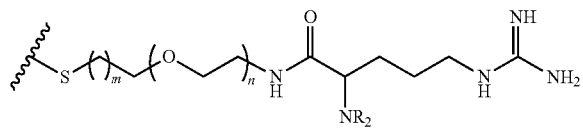

or a salt thereof, wherein m is about 0 to about 1,000 and n is about 0 to about 1,000; wherein the nanoparticle-stabilized nanocapsule has a largest dimension of about 50 nm to about 500 nm, the nanoparticle-stabilized nanocapsule has about 2 to about 100,000 of the nanoparticles, each of the nanoparticles has a largest dimension of about 1 nm to about 200 nm, and each of the nanoparticles has about 1 to about 10,000 of the amine-containing ligands; and delivering at least some of the siRNA into the cell from the nanoparticle-stabilized nanocapsule.

In certain embodiments of the method, substantially all of the siRNA from the nanoparticle-stabilized nanocapsule are delivered into the cell.

In yet another aspect, the invention generally relates to a method of forming a nanoparticle-stabilized nanocapsule. The method includes: combining a plurality of nanoparticles comprising an amine-containing ligand with one or more nucleic acid materials to form nanoparticles at least some of which are complexed with the nucleic acid material; and combining the formed nanoparticles with a nanodroplet comprising an amphiphilic fluid to form a nanoparticle-stabilized nanocapsule comprising the nanodroplet comprising the amphiphilic fluid and the formed nanoparticles on a surface of the nanodroplet.

In yet another aspect, the invention generally relates to a method of forming a nanoparticle-stabilized nanocapsule. The method includes: combining a plurality of gold nanoparticles comprising an amine-containing ligand with one or more molecules of siRNA to form nanoparticles at least some of which are complexed with the siRNA, the amine containing ligand having the structure:

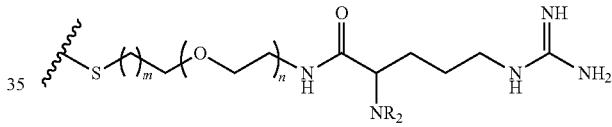

or a salt thereof, wherein m is about 0 to about 1,000 and n is about 0 to about 1,000; and combining the formed nanoparticles with a nanodroplet comprising a fatty acid to form a nanoparticle-stabilized nanocapsule comprising the nanodroplet comprising the fatty acid and the formed nanoparticles on a surface of the nanodroplet. The nanoparticle-stabilized nanocapsule has a largest dimension of about 50 nm to about 500 nm, the nanoparticle-stabilized nanocapsule has about 2 to about 100,000 of the nanoparticles, each of the nanoparticles has a largest dimension of about 1 nm to about 200 nm, and each of the nanoparticles has about 1 to about 10,000 of the amine-containing ligands.

In yet another aspect, the invention generally relates to a kit for forming a nanoparticle-stabilized nanocapsule. The kit includes: an amphiphilic fluid; and a plurality of nanoparticles comprising an amine-containing ligand configured to be combined with one or more nucleic acid materials to form nanoparticles at least some of which are complexed with the nucleic acid material, the formed nanoparticles sufficient for combining with a nanodroplet comprising the amphiphilic fluid to form a nanoparticle-stabilized nanocapsule comprising the nanodroplet comprising the amphiphilic fluid and the formed nanoparticles on a surface of the nanodroplet. In certain embodiments, the kit further includes the nucleic acid materials.

EXAMPLES

Various embodiments of the present invention can be better understood by reference to the following Examples that are offered by way of illustration. The present invention is not limited to the Examples given herein.

The examples demonstrate the use of NPSC for the direct cytosolic delivery of siRNA. siRNA was complexed with cationic arginine-functionalized gold nanoparticles via electrostatic interactions, with the resulting ensemble self-assembled onto the surface of fatty acid nanodroplets to form NPSC/siRNA nanocomplex. The complex rapidly delivered siRNA into cytosol via membrane fusion, a mechanism supported by cellular uptake studies. Using destabilized green fluorescent protein (deGFP) as a target, 90% knockdown was observed in HEK293 cells. Moreover, the delivery of siRNA targeting polo-like kinase 1(siPLK1) efficiently silenced PLK1 expression in cancer cells with concomitant cytotoxicity.

FIG. 1(a)-1(d) illustrates preparation and characterization of NPSC/siRNA. Briefly, a template emulsion was prepared by homogenizing arginine functionalized gold nanoparticle (Arg-AuNP) with linoleic acid in 5 mM phosphate buffer (pH=7.4). The template emulsion was transferred to Arg-AuNP solution and incubated for additional 10 min. to afford stabilized NPSC. The NPSC was then mixed with siRNA at different molar ratios and incubated at room temperature for 15 min., followed by gel electrophoresis assay and Ribogreen assay to measure siRNA encapsulation.

As shown in FIG. 1b, with NPSC to siRNA molar ratio increased from $1.1 \times 10^{-4}$ to $11 \times 10^{-4}$, the migration of siRNA on the gel was gradually retarded. The binding at molar ratio of $5.5 \times 10^{-4}$ completely retarded siRNA from migration, with 91±2% of siRNA encapsulation, as determined by Ribogreen assay. This optimized NPSC to siRNA binding ratio was fixed for all subsequent intracellular delivery experiment. The encapsulation of siRNA had negligible effect on the morphology of NPSC, as revealed by transmission electron microscopy (TEM) (FIG. 1c). Dynamic light scattering (DLS) indicated NPSC and NPSC/siRNA formed nanoparticles with size at 149±5 nm and 179±8 nm in diameter, respectively (Table 1). The slightly increased size of NPSC/siRNA compared to that of NPSC is consistent with swelling arising from the encapsulation of siRNA onto the NPSC surface. Additionally, the zeta potential of NPSC was made more negative from −25.5 mV to −39.4 mV for NPSC/siRNA complex, confirming the successful encapsulation of siRNA into NPSC.

TABLE 1

Dynamic light scattering (DLS) measurements of size (number average), polydisperse index (PDI), and zeta potential of NPSC and NPSC/siRNA complex

|  | NPSC | NPSC/siRNA |
|---|---|---|
| Hydrodynamic Diameter (nm) | 149 ± 5 | 179 ± 8 |
| PDI | 0.11 ± 0.01 | 0.19 ± 0.005 |
| Zeta Potential (mV) | −25.5 ± 0.7 | −39.4 ± 1.3 |

The encapsulation of siRNA into NPSC efficiently protected siRNA against nuclease degradation, a prerequisite for the intracellular delivery of siRNA. As shown in FIG. 1d, the treatment of free siRNA with Ribonuclease A (RNase A, 7 mU) for 1 h resulted in a complete degradation of siRNA. However, significant amounts of siRNA were still detected after the treatment of NPSC/siRNA complex even at a much higher RNase A amount (35 mU) and a longer incubation (2 h). Similarly, the NPSC/siRNA complex efficiently protected siRNA against serum degradation (FIGS. 2(a)-2(b)). The enhanced enzymatic stability of siRNA with NPSC encapsulation may be ascribed to steric protection and neutralization of siRNA charge, which together decreased the susceptibility of siRNA toward nuclease degradation.

Figure 2A:
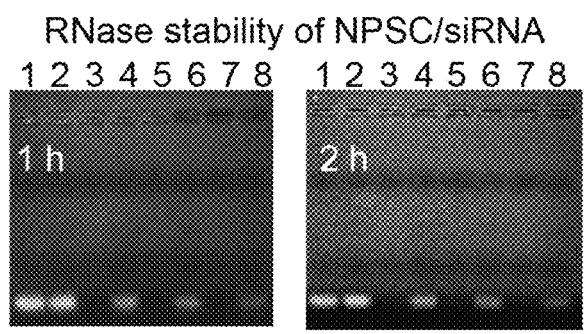
FIGS. 2(a)-2(b) illustrate agarose gel electrophoresis assay of NPSC protected siRNA from degradation: (a) NPSC protected siRNA from RNase A digestion. siRNA or NPSC/siRNA complex were incubated with indicated amount of RNase A for 1 and 2 h. (b) Serum stability of NPSC/siRNA. siRNA or NPSC/siRNA complex were incubated with 10% FBS at 37° C. for indicated time before electrophoresis.
Figure 2B:
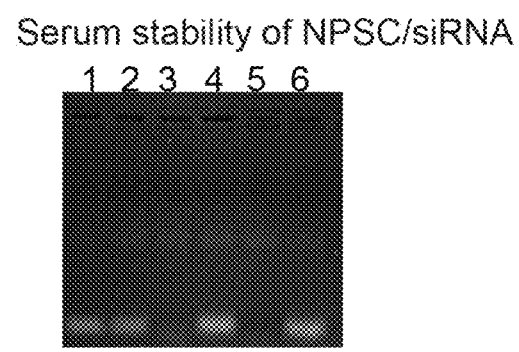

NPSC complex was prepared encapsulating fluorescently labeled siRNA (Cy3-siRNA) with a scrambled sequence to evaluate delivery of siRNA. The cellular uptake and subcellular localization of NPSC/siRNA complex was then monitored using confocal laser scanning microscopy (CLSM). Significant intracellular accumulation of red fluorescence occurred when the cells were treated with NPSC/Cy3-siRNA complex (FIG. 4(a)). Significantly, the Cy3 fluorescence was evenly distributed within whole cell, and with little overlap with the endosome/lysosome by using LysoTracker@Green counter-staining. These CLSM studies indicate that the NPSC/siRNA complex was able to transport siRNA directly into cytosol without endosome/lysosome entrapment associated with polymer or lipid-based siRNA delivery vehicles. NPSC mediated siRNA uptake is siRNA concentration-dependent. With the Cy-3 siRNA increased from 12 nM to 36 nM, the Cy3 fluorescence intensity increased up to ten-fold, and >70% cells were Cy-3 fluorescence positive, as measured by flow cytometry analysis (FIG. 3). FIGS. 2(a)-2(b) illustrate agarose gel electrophoresis assay of NPSC protected siRNA from degradation.

Figure 3A:
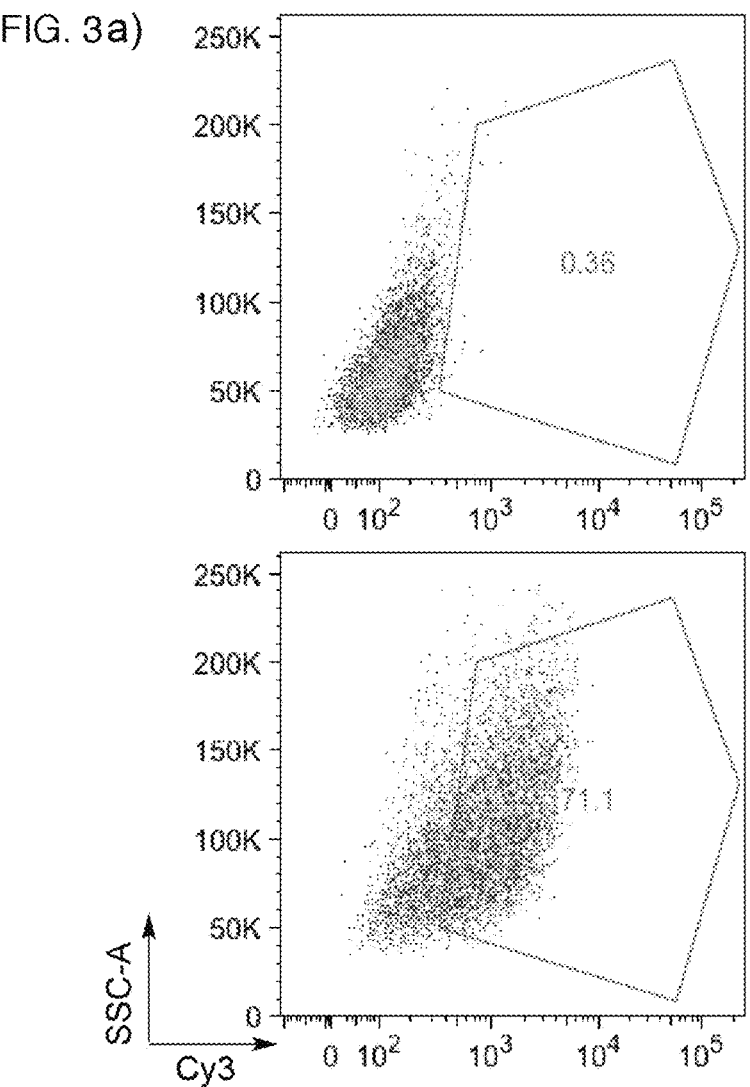
FIGS. 3(a)-3(b) illustrate a cellular uptake study of NPSC/Cy3-siRNA complex: (a) Representative flow cytometry plots of Cy3-siRNA positive HeLa cells. HeLa cells without NPSC/Cy3-siRNA (up) and with 36 nM NPSC/Cy3-siRNA (bottom) treatment were harvested for flow cytometry analysis. (b) siRNA dose-dependent cellular uptake. HeLa cells were treated with NPSC/Cy3-siRNA containing varied concentration of siRNA for 4 h. The error bars represent the standard deviations of three parallel measurements.
Figure 3B:
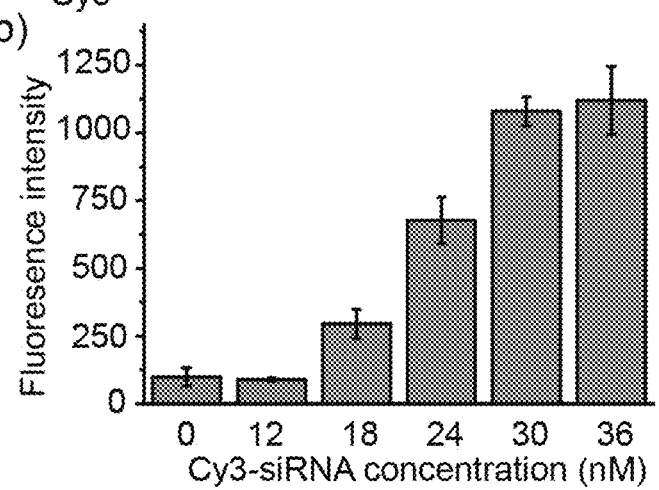

FIGS. 3(a)-3(b) depict a cellular uptake study of NPSC/Cy3-siRNA complex. The siRNA uptake and trafficking dynamics of NPSC siRNA delivery was investigated using time-lapse fluorescence imaging of Cy3-siRNA (FIG. 4(b)). With the addition of NPSC/Cy3-siRNA complex into HeLa cells, the fluorescence images of cells post-nucleic acid delivery into the cells were immediately captured at 1 min. interval. Time-lapse imaging analysis revealed that cytosolic siRNA fluorescence could be recorded within 5 min. exposure of NPSC/siRNA complex to cells, and the siRNA fluorescence was saturated after 20 min. of incubation, demonstrating extraordinary fast and efficient siRNA delivery using NPSCs. The siRNA fluorescence was evenly distributed within whole cell cytosol further demonstrating that NPSC mediated siRNA delivery enter cells bypassing endo/lysosomes.

Figure 4A:
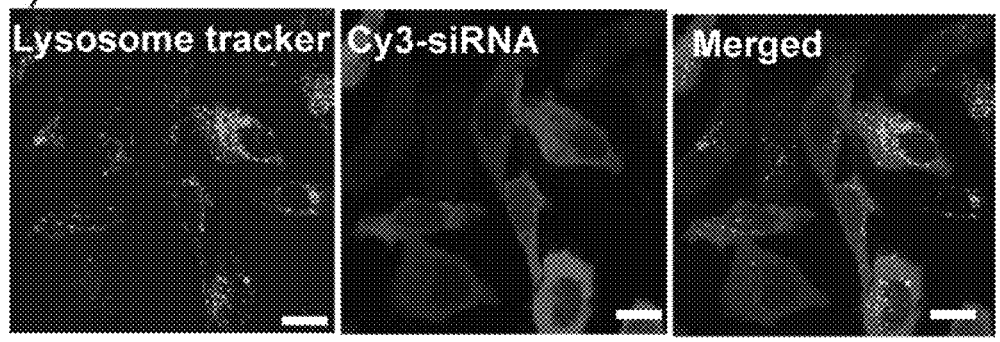
FIGS. 4(a)-4(b) illustrate cytosolic delivery of Cy3-labeled siRNA into HeLa cells: (a) Confocal microscopy images of HeLa cells after 1 hour treatment with 40 nM of NPSC/Cy3-siRNA complex. siRNA are not colocalize with endolysosomes. Endosome/lysosome was stained with LysoTracker @Green. Scale bars: 20 μm. (b) Live cell imaging of rapid Cy3-siRNA release into the cytosol of HeLa cell by NPSC. "0 min" label represents the starting point of release. Scale bars: 20 μm.
Figure 4B:
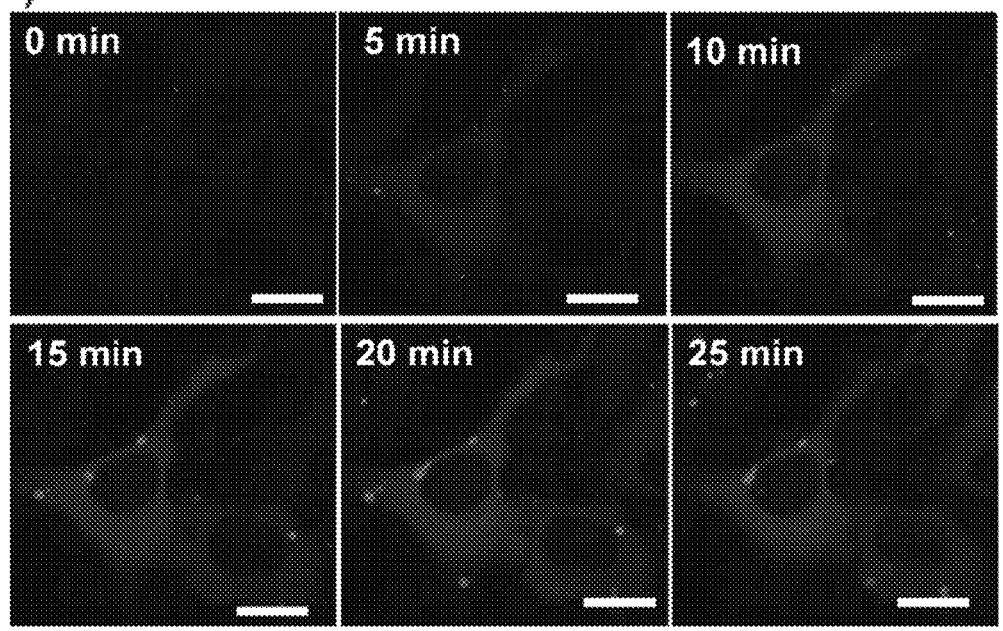

FIGS. 4(a)-4(b) illustrate cytosolic delivery of Cy3-labeled siRNA into HeLa cells.

In a previous study on protein delivery it was observed a similar even cytosolic distribution of GFP, prompting us to hypothesize that a membrane fusion process was operative. While there is circumstantial evidence of this mechanism, further studies were performed to test this hypothesis. The efficiency of membrane fusion-mediated uptake is dependent on the cholesterol level in cell membrane.

To study whether NPSC delivered siRNA in a membrane fusion pathway, HeLa cells were pre-treated with nystatin (100 μg/mL) an inhibitor that has been used to deplete cholesterol from the plasma membrane, prior to delivery of siRNA to the cells. Meanwhile, FITC-labeled dextran, known to enter cells via endocytic pathways, was co-incubated with cells to exclude the potential effect of nystatin treatment on endocytosis. Nystatin has no effect on the stability of NPSC/siRNA complex, as revealed by the DLS size of NPSC/siRNA complex in the presence and absence of nystatin (FIG. 5).

Figure 7A:
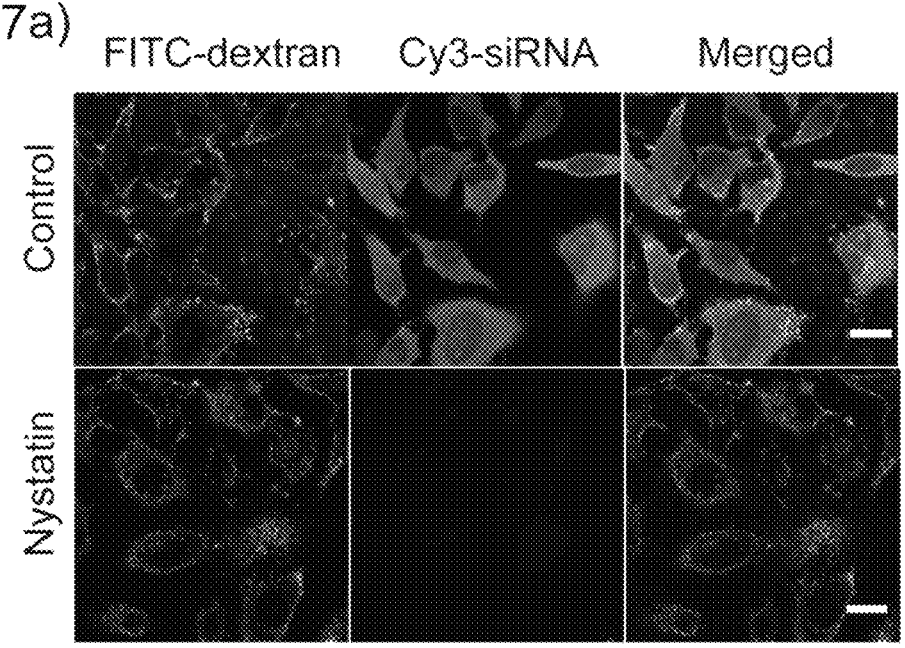
FIGS. 7(a)-7(b) illustrate NPSC delivered siRNA through membrane fusion: (a) FITC-dextran and NPSC/Cy3-siRNA were co-incubated with HeLa cells in the absence and presence of nystatin (100 μg/mL). (b) Flow cytometry analysis of HeLa cells with NPSC/Cy3-siRNA treatment at 37° C., or at 4° C., or with a pre-treatment of dynasore (80 μM). The error bars represent the standard deviations of three parallel measurements.
Figure 7B:
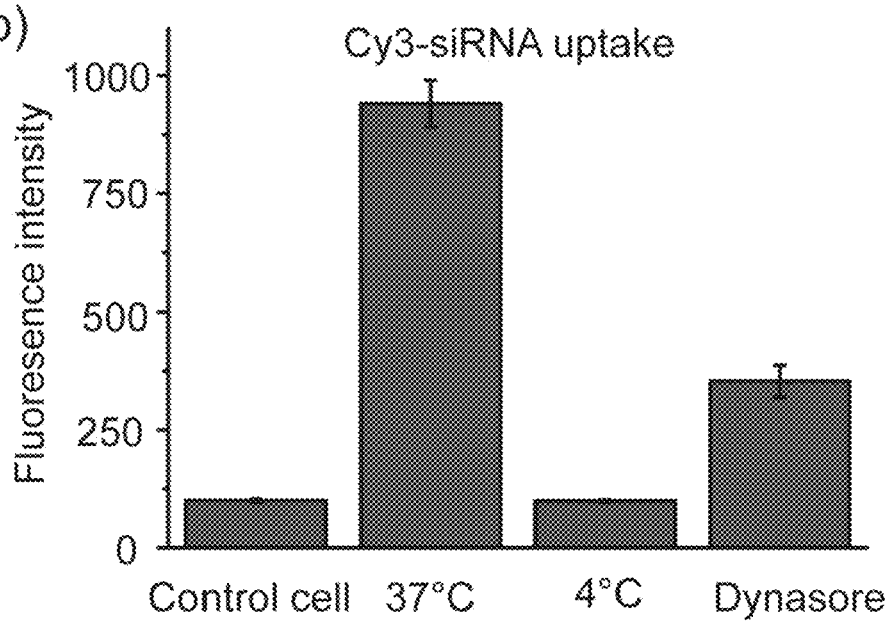

The siRNA and FITC-dextran uptake was then monitored by CLSM imaging. As shown in FIG. 3A, both dextran and NPSC/siRNA efficiently enter HeLa cells in the absence of nystatin, with low co-localization observed between dextran and siRNA, confirming non-endocytic uptake of NPSC/siRNA complex. The treatment of nystain significantly blocked siRNA uptake, however, no uptake inhibition was observed for FITC-dextran. The siRNA uptake inhibition by nystatin treatment was further confirmed and quantified by flow cytometry analysis (FIG. 6). Nystatin pre-treatment significantly decreased the siRNA fluorescence intensity of HeLa cells; the weak Cy3 fluorescence could be ascribed to the non-specific binding of NPSC/siRNA complex on cell surface, as confirmed by z-stack CLSM imaging of NPSC/siRNA uptake (FIG. 6). The above results indicated that nystain treatment had not blocked the endocytosis of FITC-dextran, but inhibited the membrane fusion of siRNA by depleting cell membrane cholesterol.

siRNA uptake efficiency was studied by studying uptake at reduced temperatures and by inhibiting dynamin. HeLa cells were pre-treated at 4° C. for 30 min. before the exposure of NPSC/Cy3-siRNA, the siRNA uptake was quantified by flow cytometry analysis and compared to that at 37° C. As shown in FIG. 7($b$), Cy3 fluorescence arising from siRNA uptake was significantly decreased for cells with 4° C. pre-treatment, similar to previous reports that the membrane fusion process is a temperature dependent process. Meanwhile, the treatment of HeLa cells with dynasore (80 µM), an inhibitor of dynamin that regulates membrane fusion by expanding the fusion pores, similarly reduced the cellular uptake of siRNA (FIG. 7($b$)). Taken together, the above cellular uptake studies indicate that NPSC facilitated cytosolic siRNA delivery is a cholesterol dependent membrane fusion process.

Figure 8:
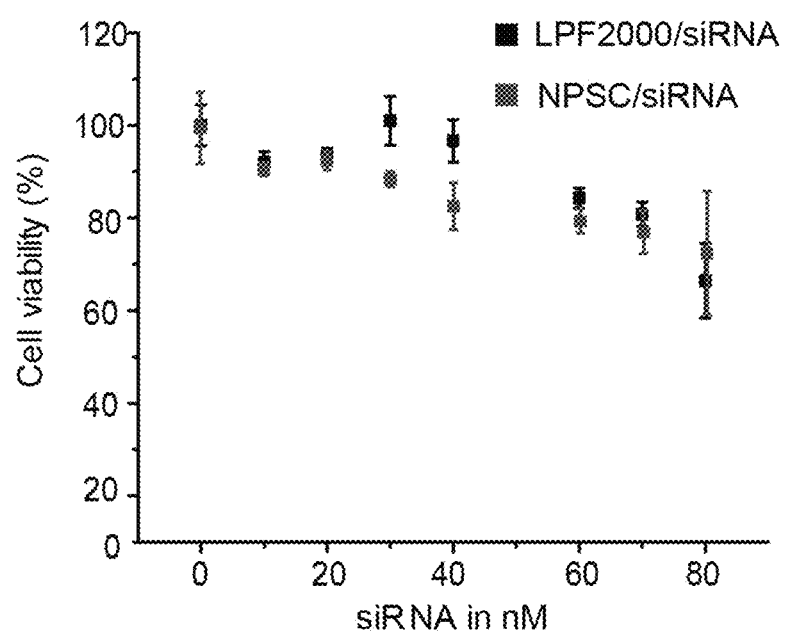
FIG. 8 illustrates viability of deGFP-HEK293 cells treated with NPSC/siRNA (red square) or Lipofectamine 2000/siRNA (black square) complexes. Scrambled siRNA was used to complex with NPSC or Lipofectamine 2000. The error bars represent the standard deviations of three parallel measurements.

The biocompatibility of the NPSC/siRNA delivery platform was next evaluated by treating destabilized green fluorescent protein expressing deGFP-HEK293 cells with varied concentrations of NPSC/siRNA complexes, followed by cell viability assay. With siRNA concentrations (complexed with NPSC) from 10 nM to 60 nM the cells retained viabilities >80% (FIG. 8), with the biocompatibility of NPSCs comparable to that of a commercial reagent for transfection, Lipofectamine 2000 (FIG. 8).

Having demonstrated the efficient yet safe cytosolic delivery of siRNA using NPSC, we next investigated the efficacy of NPSC-facilitated siRNA delivery to knock down targeted genes. As many disease-related proteins have short half-lives inside cells, an efficient siRNA delivery to silence the gene of short half-life would have high therapeutic index. In this study, destabilized GFP (deGFP) with a half-life around 2 h was chosen as a testbed target gene. Stable-expressing deGFP-HEK293 cells were treated with NPSC/siRNA complex targeting deGFP (NPSC/si_deGFP) or a scrambled siRNA (NPSC/siScr), the deGFP expression profiles were monitored by CLSM imaging and flow cytometry analysis.

Figure 11A:
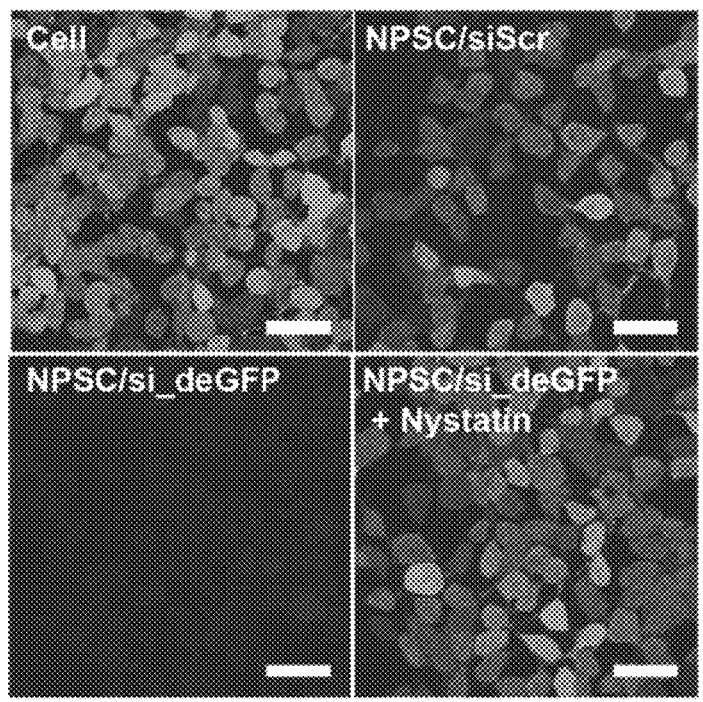
FIGS. 11(a)-11(b) illustrate that NPSC/siRNA delivery silenced the deGFP expression of deGFP-HEK293 cells: (a) Confocal microscopy images of deGFP-HEK 293 cells without siRNA transfection (top left), with 60 nM of NPSC/siScr (top right), with 60 nM of NPSC/si_deGFP (bottom left) and with 60 nM of NPSC/si_deGFP with nystatin pre-treatment (bottom right). Scale bars: 40 μm. (b) Quantification of deGFP expression of deGFP-HEK 293 cells without treatment (black), with naked si_deGFP (purple), NPSC/siScr (magenta), NPSC/si_deGFP (red), Lipofectamine 2000 (LPF2K)/si_deGFP (blue), and NPSC/si_deGFP with nystatin pretreatment (green). 60 nM of siGFP or scrambled siRNA was used for transfection. The fluorescence intensity was measured by flow cytometry analysis and normalized to cells without treatment. The error bars represent the standard deviations of three parallel measurements.
Figure 11B:
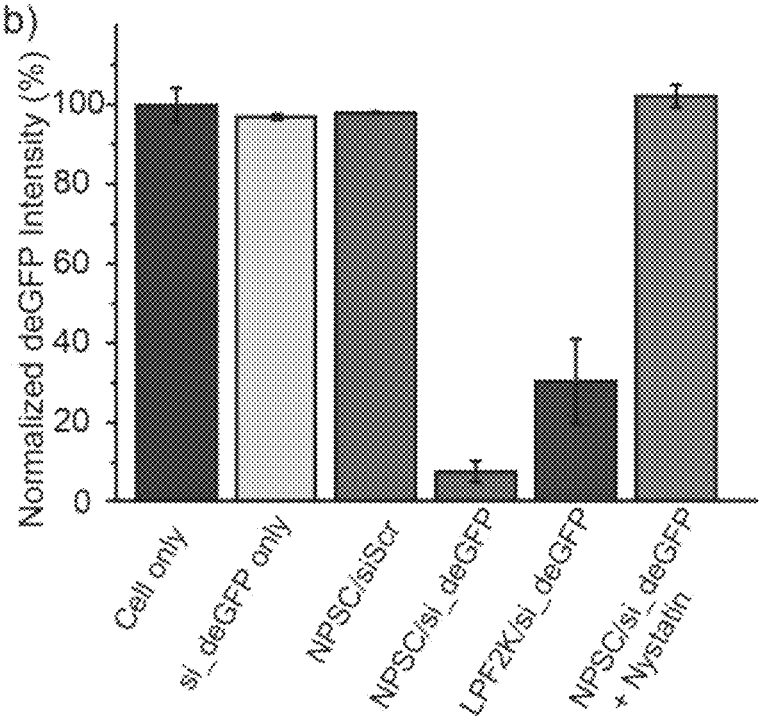

As shown in FIG. 4$a$, only very faint fluorescence signal was observed in the CLSM images when the cells were treated with NPSC/si_deGFP complex, indicating the high efficiency of NPSC mediated deGFP knockdown. Flow cytometry analysis revealed that the NPSC/siRNA complex treatment (with 60 nM of si_deGFP) silenced the deGFP expression down to a level below 10% of blank control (FIG. 4$b$ and FIG. 9($a$)). This gene silencing efficiency is substantially superior to the commercial lipid-based reagents for transfection, Lipofectamine 2000 (LPF2K, FIG. 4$b$) and RNAi Max (FIG. 10). The NPSC/si_deGFP complex silenced deGFP genes in a siRNA concentration dependent manner. With siRNA concentration increased from 20 nM to 60 nM the deGFP expression was gradually suppressed from 90% down to 10% of blank controls (FIG. 9($b$)). No gene silencing was observed when the cells were treated with either naked si_deGFP or an NPSC/siRNA complex with a scrambled sequence (FIG. 11($b$)).

As NPSC delivered siRNA via a membrane fusion pathway, it was hypothesized that the pre-treatment of HEK cells with nystatin to deplete cholesterol could block siRNA uptake and gene silencing. The GFP gene knockdown efficiency of HEK cells with nystatin pre-treatment, followed by NPSC/side GFP treatment, was significantly decreased, as indicated by the strong fluorescence in CLSM images (FIG. 11($a$)) and minor GFP gene knockdown in the flow cytometry analysis (FIG. 11($b$)). The GFP gene silencing results again confirmed that NPSC facilitated siRNA is a cholesterol-dependent membrane fusion process, and the cytosolic siRNA delivery is superior to commercial reagents in terms of gene silencing efficiency.

Figure 12A:
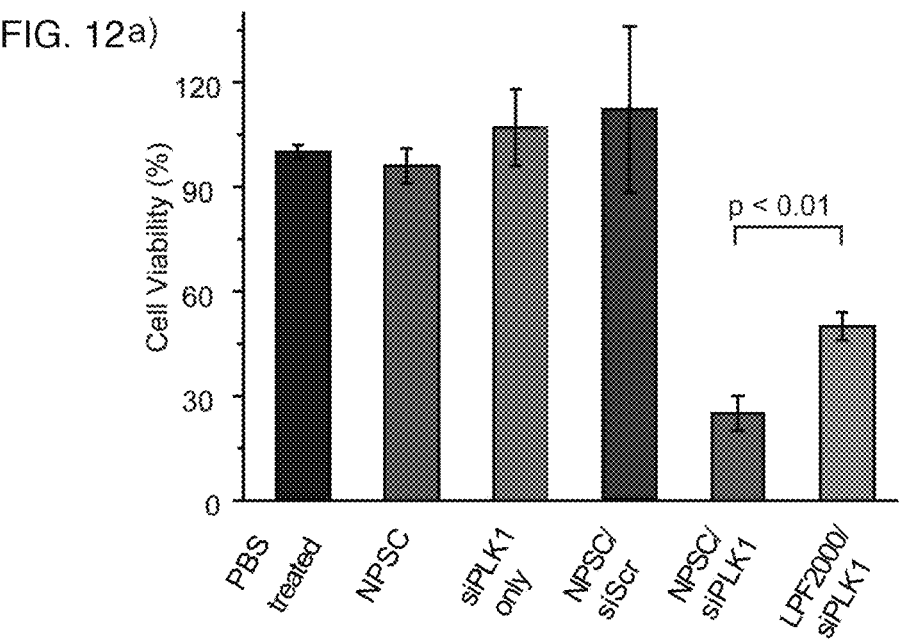
FIGS. 12(a)-12(b) illustrate NPSC mediated siPLK1 delivery in MDA-MB-231 cells: (a) Cell viability of MDA-MB-231 cells treated with NPSC/siPLK1 or scrambled siRNA (40 nM). For the Lipofectamine 2000 control, 40 nM of siPLK1 was complexed with LPF2000 according to manufacturer's instructions. The cell viability was determined using Alamar Blue assay 48 h post-transfection. (b) Representative PLK1 protein expression of MDA-MB-231 cells determined by Western blot analysis after incubation with 40 nM siPLK1 in NPSC/siPLK1 and controls. GAPDH expression was measured in all the samples to serve as an internal control.
Figure 12B:
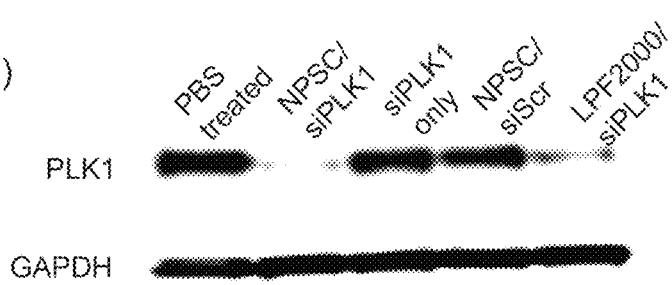
Figure 13:
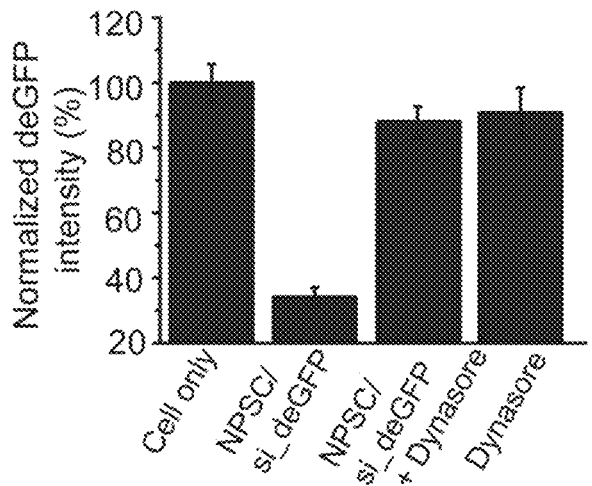
FIG. 13 illustrates quantification of deGFP expression of deGFP-HEK 293 cells without treatment, with NPSC/si_deGFP, NPSC/si_deGFP with dynasore pretreatment (80 μm), and with only dynasore pretreatment (80 μm); 36 nM of si_deGFP was used.
Figure 14:
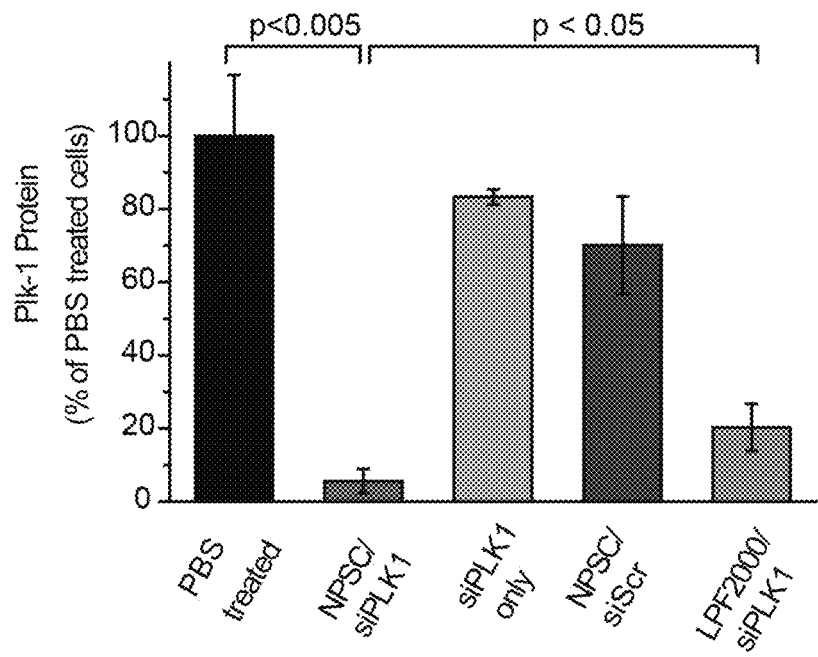
FIG. 14 illustrates an analysis of band intensities of PLK1 protein expression presented as the ratio of PLK1 to GAPDH in western blot image.

When studying the delivery of therapeutic siRNA was studied, Polo-like kinase 1 (PLK1) was selected as a model therapeutic target. PLK1 is a key regulator of mitotic progression of cells, and is up-regulated in many types of cancer cells. Inhibition of PLK1 activity or the depletion of PLK1 protein can induce mitotic arrest and prevent tumor cell proliferation. Treatment of MDA-MB-231 cells with 40 nM NPSC/siPLK1 reduced cell viability to 30% whereas no change in viability was observed with naked or NPSC/siRNA scrambled controls (FIG. 12($a$)). Significantly, NPSC/siPLK1 inhibited cell proliferation with a higher efficiency than that of LPF2000. Knockdown of intracellular PLK1 protein was determined by western blot analysis. Essentially complete knockdown was observed when MDA-MB-231 cells were treated with NPSC/siPLK1 (40 nM siRNA) (FIG. 12($b$)), with protein expression decreased by ~95% (FIG. 13), significantly greater knockdown than LPF2000/siPLK1 complexes. FIG. 14 illustrates an analysis of band intensities of PLK1 protein expression presented as the ratio of PLK1 to GAPDH in western blot image.

Figure 15A:
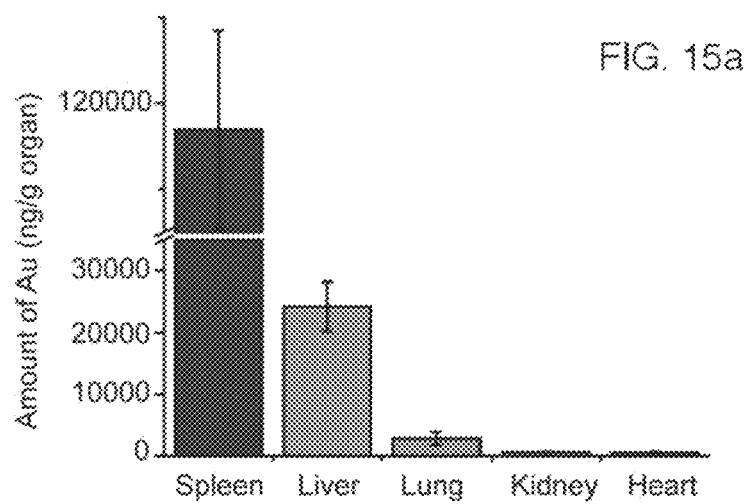
FIG. 15 illustrates biodistribution of Au in mouse organs after intravenous injection of NPSC/siRNA. The amount of Au was quantitatively analyzed by ICP-MS, and Au concentrations were calculated by dividing gold amount (ng) by organ weight (g) (n=3, mean±standard deviation).
Figure 15B:
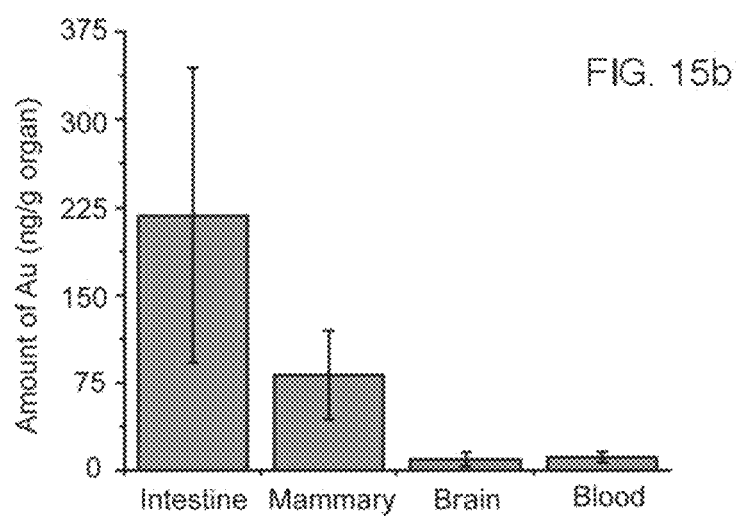

FIG. 15 illustrates biodistribution of Au in mouse organs after intravenous injection of NPSC/siRNA. The amount of Au was quantitatively analyzed by ICP-MS, and Au concentrations were calculated by dividing gold amount (ng) by organ weight (g) (n=3, mean±standard deviation).

Figure 16:
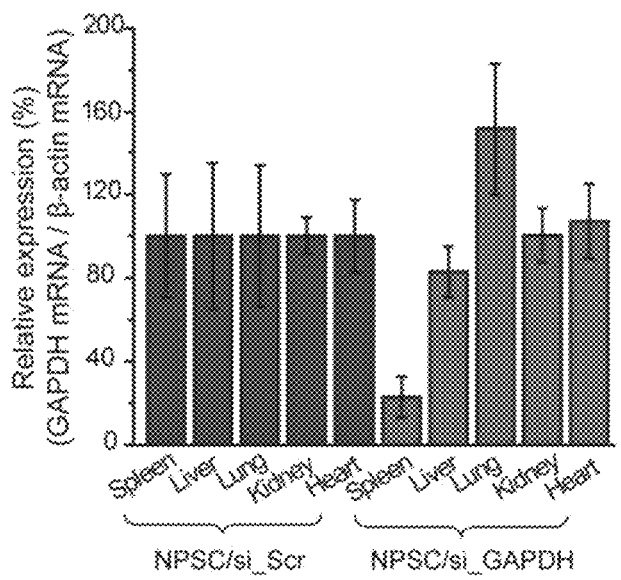
FIG. 16 illustrates in vivo delivery of NPSC/si_GAPDH effectively decreased splenic GAPDH mRNA levels. BALB/c mice were i.v. injected twice with NPSC/siRNA complexes at a siRNA dose of 0.14 mgkg$^{-1}$ at 2 days interval, and organs were harvested 3 days post final injection. All GAPDH mRNA measurement was normalized to β-actin, with the NPSC/si_GAPDH values presented relative to the NPSC/si_Scr controls (n=3).

FIG. 16 illustrates in vivo delivery of NPSC/si_GAPDH effectively decreased splenic GAPDH mRNA levels. BALB/c mice were i.v. injected twice with NPSC/siRNA complexes at a siRNA dose of 0.14 mgkg$^{-1}$ at 2 days interval, and organs were harvested 3 days post final injection. All GAPDH mRNA measurement was normalized to β-actin, with the NPSC/si_GAPDH values presented relative to the NPSC/si_Scr controls (n=3).

Figure 17:
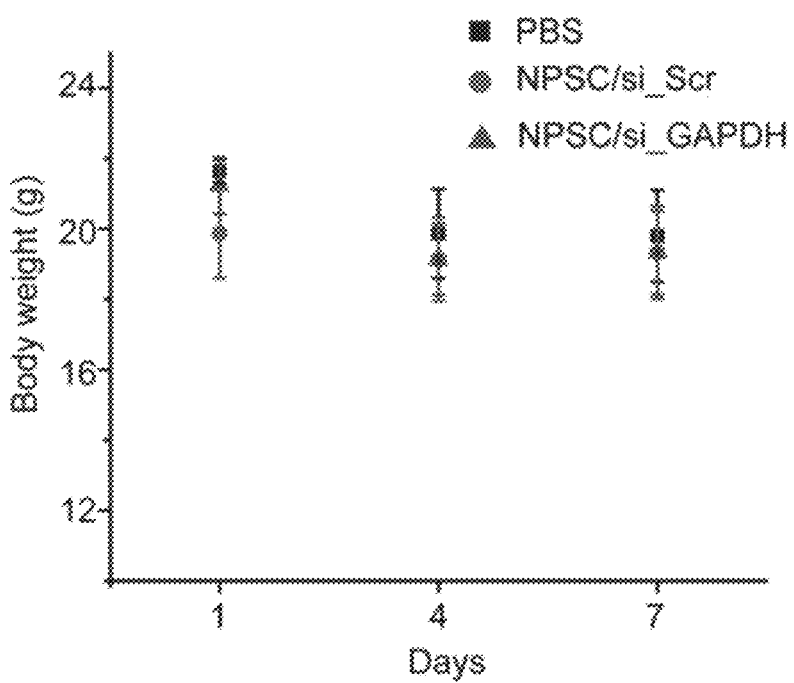
FIG. 17 illustrates average mouse weight changes during the course of treatment with PBS, NPSC/si_Scr, and NPSC/si_GAPDH (n=3, mean±standard deviation).

FIG. 17 illustrates average mouse weight changes during the course of treatment with PBS, NPSC/si_Scr, and NPSC/si_GAPDH (n=3, mean±standard deviation).

Figure 18:
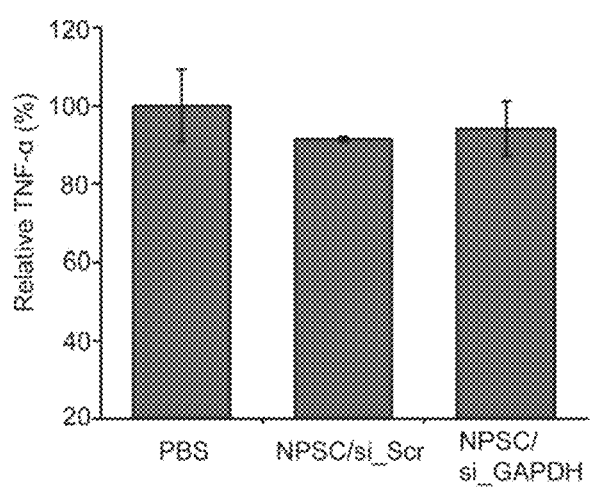
FIG. 18 illustrates serum TNF-α level following the injection of PBS, NPSC/si_Scr, and NPSC/si_GAPDH. No significant change in serum TNF-α level following the injection of PBS, NPSC/si_Scr, and NPSC/si_GAPDH. The TNF-α level was measured using the ELISA kits (R&D systems, MN), and normalized to the PBS treated group (n=3, mean±standard deviation).

FIG. 18 illustrates serum TNF-α level following the injection of PBS, NPSC/si_Scr, and NPSC/si_GAPDH. No significant change in serum TNF-α level following the injection of PBS, NPSC/si_Scr, and NPSC/si_GAPDH. The TNF-α level was measured using the ELISA kits (R&D systems, MN), and normalized to the PBS treated group (n=3, mean±standard deviation).

Figure 19:
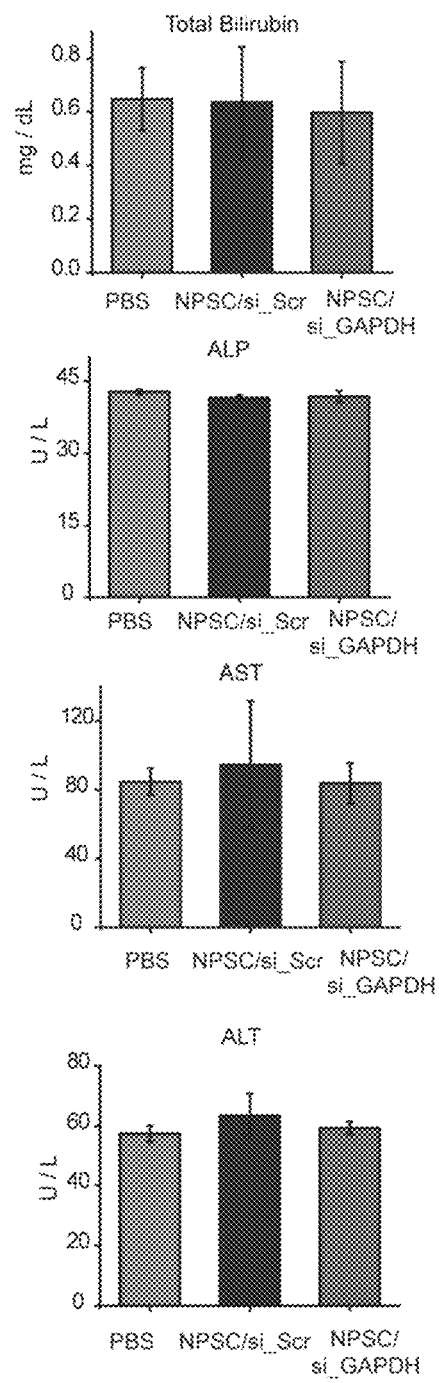
FIG. 19 illustrates clinical chemistry parameters. Parameters were evaluated for negative control (PBS), NPSC/si_Scr, and NPSC/si_GAPDH groups of BALB/c mice. The mice had been i.v. injected with with NPSC/siRNA complexes at a siRNA dose of 0.14 mgkg$^{-1}$ at 2 days interval. Blood was drawn for analysis 72 hours post-final injection. There were no statistically significant changes in any of the clinical chemistry parameters for any of the treated groups compared to controls. Normal ranges for clinical chemistry parameters are: total bilirubin (0-0.9 mg/dL), alkaline phosphatase (ALP: 44-147 U/L), aspartate aminotransferase (AST: 54-298 U/L), and alanine aminotransferase (ALT: 17-77 U/L). Error bars represent standard deviation (n=3).

FIG. 19 illustrates clinical chemistry parameters. Parameters were evaluated for negative control (PBS), NPSC/si_Scr, and NPSC/si_GAPDH groups of BALB/c mice. The mice had been i.v. injected with with NPSC/siRNA complexes at a siRNA dose of 0.14 mgkg$^{-1}$ at 2 days interval. Blood was drawn for analysis 72 hours post-final injection. There were no statistically significant changes in any of the clinical chemistry parameters for any of the treated groups compared to controls. Normal ranges for clinical chemistry parameters are: total bilirubin (0-0.9 mg/dL), alkaline phosphatase (ALP: 44-147 U/L), aspartate aminotransferase (AST: 54-298 U/L), and alanine aminotransferase (ALT: 17-77 U/L). Error bars represent standard deviation (n=3).

Figure 20:
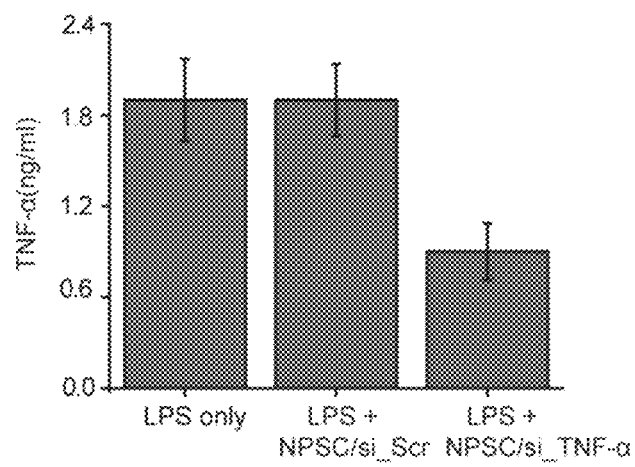
FIG. 20 illustrates in vivo delivery of NPSC/si_TNF-α effectively decreased serum TNF-α production from LPS-induced inflammation. BALB/c mice were i.v. injected twice with NPSC/siRNA complexes at a siRNA dose of 0.28 mgkg$^{-1}$ at 6 hours interval, followed by LPS (5 mg/kg, i.p.) 24 hours later. Serum TNF-α was measured by ELISA 1.5 hours after administration of LPS. LPS, lipopolysaccharide; TNF-α, tumor necrosis factor-α.

FIG. 20 illustrates in vivo delivery of NPSC/si_TNF-α effectively decreased serum TNF-α production from LPS-induced inflammation. BALB/c mice were i.v. injected twice with NPSC/siRNA complexes at a siRNA dose of 0.28 mgkg$^{-1}$ at 6 hours interval, followed by LPS (5 mg/kg, i.p.) 24 hours later. Serum TNF-α was measured by ELISA 1.5 hours after administration of LPS. LPS, lipopolysaccharide; TNF-α, tumor necrosis factor-α.

Figure 21:
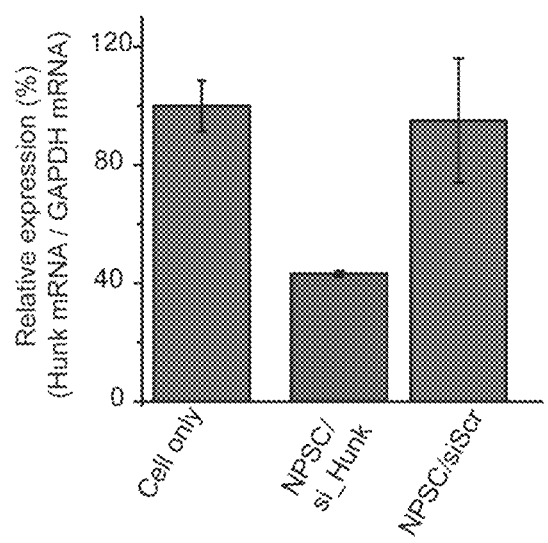
FIG. 21 illustrates qtPCR of Hunk mRNA levels normalized against GAPDH of MCF-7 cells 48 hours after treatment of medium (control), NPSC/siScr (Scr: 30 nM), NPSC/si_Hunk (si_Hunk: 30 nM). The error bars represent the standard deviations of three parallel measurements.

FIG. 21 illustrates qtPCR of Hunk mRNA levels normalized against GAPDH of MCF-7 cells 48 hours after treatment of medium (control), NPSC/siScr (Scr: 30 nM), NPSC/si_Hunk (si_Hunk: 30 nM). The error bars represent the standard deviations of three parallel measurements.

FIG. 22 illustrates qtPCR of survivin mRNA levels normalized against GAPDH of MCF-7 cells 48 hours after treatment of medium (control), NPSC/siScr (Scr: 40 nM), NPSC/si_Survivin (si_Survivin: 40 nM). The error bars represent the standard deviations of three parallel measurements.

FIGS. 23(a)-23(b) illustrates: (a) Flow cytometry plots of Cy3-siRNA positive RAW 264.7 cells. RAW 264.7 cells without NPSC/Cy3-siRNA (top) and with 40 nM NPSC/Cy3-siRNA (bottom) treatment were harvested for flow cytometry analysis. (b) siRNA dose dependent cellular uptake. c) NPSC/siRNA delivery silenced the TNF-α expression of lipopolysaccharide-stimulated RAW 264.7 macrophages, as shown by ELISA. The error bars represent the standard deviations of three parallel measurements.

In summary, NPSC/siRNA complexes provided a highly effective delivery of siRNA into cells. Microscopy studies showed that these systems delivered siRNA directly to the cytosol, providing efficient utilization of the siRNA payload by avoiding endosomal sequestration. In addition, it was proved that such a direct cytosolic siRNA delivery was a temperature-dependent membrane fusion process.

EXPERIMENTAL

General

All reagents or chemicals used were purchased from Fisher Scientific or Sigma-Aldrich. Chloroauric acid used for gold nanoparticle synthesis was bought from Strem Chemicals Inc. (Newburyport, Mass.). siRNA targeting deGFP (si_deGFP, sense strand AUGAUAUAGACGUU-GUGGC) (SEQ ID NO:1) and siRNA targeting Polo-like kinase 1 (siPLK1, sense strand sequence GUCUCAAGGC-CUCCUAAUA) (SEQ ID NO:2) were purchased from Sigma-Aldrich. Scrambled siRNA (sense strand sequence UUCUCCGAACGUGUCACGU) (SEQ ID NO:3) and Cy3 labeled scrambled siRNA, Lipofectamine 2000 and RNAi Max transfection reagent, and LysoTracker® Green DND-26 were all purchased from Invitrogen (Carlsbad, Calif.). Fluorescein isothiocyanate-Dextran (MW 70,000) used for cellular uptake study was obtained from Sigma-Aldrich. Transmission electron microscopy (TEM) was performed on a JEOL-2010 microscope with an accelerating voltage of 200 kV. Particle size was measured on a Malvern Zetasizer (Nano series, Malvern Instruments Inc, USA) with a He—Ne laser (633 nm) and a backscattering angle of 173°. Confocal microscopy images were obtained on a Zeiss LSM 510 Meta microscope (Carl Zeiss, Jena, Germany) using a 63× or 40× objective. Flow cytometry analysis was performed on a BD LSR-II flow cytometer equipped with FACSDiva (BD Sciences, USA) by counting 10000 events.

NPSC and siRNA Complexation and Gel Electrophoresis

The arginine-functionalized AuNP (Arg-AuNP) and NPSC were synthesized according to our previous report. (Yang, et al. *Angew. Chem.* 2011, 123, 497-501; *Angew. Chem. Int. Ed.* 2011, 50, 477-481.) Briefly, 1 μL of linoleic acid was mixed with 500 μL of phosphate buffer (5 mM, pH=7.4) containing 1 μM Arg-AuNP and agitated by an amalgamator at 5000 rpm for 100 s to form emulsions. Then, 10 μL of the emulsion was added into 90 μL of 5 mM phosphate buffer containing 2.5 μM Arg-AuNP and incubated for 10 min. at room temperature to afford NPSC. To optimize the condition for siRNA encapsulation, 5 pmol siRNA was mixed with NPSC at different molar ratios (The concentration of NPSC was calculated according to reported method) for 20 min., and then subject to electrophoresis on an agarose gel (0.8% w/v) for 30 min. at 120 mV in TAE buffer (40 mM Tris-HCl, 1% v/v acetic acid, 1 mM EDTA). (Yang, et al. *Angew. Chem.* 2011, 123, 497-501; *Angew. Chem. Int. Ed.* 2011, 50, 477-481.) To evaluate the protection of siRNA against RNase A digestion, 5 pmol of free siRNA or NPSC/siRNA complex was incubated with varied amount of RNase A at 37° C. At the indicated times, the enzymatic reaction was stopped by adding sodium dodecyl sulfate to denature RNase A at 60° C. for 5 min. To above reaction mixture was added heparin solution, followed by another 10 min. incubation to displace siRNA from NPSC, the samples were then analyzed by electrophoresis on agarose gels (0.8% w/v). For NPSC/siRNA serum stability study, 5 pmol of NPSC/siRNA complex was incubated in 10 uL PB (5 mM, pH=7.4) containing 10% FBS at 37° C. for 1 h and 2 h. The nucleases in FBS were denatured by adding 1 uL 50 mM SDS solution, followed by an additional 5 min. of incubation at 60° C. The siRNA was released from NPCS/siRNA complex by adding 1 uL of 50 mg/mL heparin solution. The above samples were then assayed by electrophoresis by using 0.8% agarose gel as we described above.

Cell Culture

HeLa cells and MDA-MB-231 cells were purchased from American Type Culture Collection (ATCC, Manassas, Va.). deGFP expressing HEK293 cells were a generous gift from Prof. Eben Alsberg (Case Western Reserve University). All cells were cultured at 37° C. under a humidified atmosphere of 5% $CO_2$. Low-glucose Dulbecco's modified Eagle's medium (DMEM, 1.0 g/L glucose, for HeLa cells), and high-glucose DMEM (4.5 g/L, for HEK293 cells and MDA-MB-231 cells) supplemented with 10% fetal bovine serum (FBS) and 1% antibiotic (100 U/mL penicillin and 100 μg/mL streptomycin) was used for cell culture.

Fluorescently Labeled Cy3-siRNA Delivery

For confocal laser scanning microscopy (CLSM) imaging of the cellular uptake of NPSC/siRNA complex, HeLa cells (2.0×10$^5$ cells) were seeded in a 35 mm glass bottom culture dish (MatTek, MA) a day before experiment. At the day of delivery, the culture medium was removed and replaced with Opti-MEM containing 40 nM NPSC/Cy3-siRNA, followed by another 2 h of incubation at 37° C. After removing medium, the cells were washed three times with cold phosphate buffer saline (PBS) for fluorescence imaging under a Zeiss LSM 710 confocal microscope. For the time-lapse live cell imaging, 2.0×10$^5$ HeLa cells were cultured in the confocal dish 24 h prior to the experiment. Before the cell imaging, cells were washed with PBS for three times, followed by the incubation with NPSC/siRNA in Opti-MEM. The confocal dish was then placed in the live cell imaging chamber with 5% $CO_2$ and at 37° C. on the confocal microscope. A series of images were taken at 1 min. intervals, and the cells were imaged for 25 min. in total.

Nystatin Treatment Inhibited siRNA Delivery

HeLa cells or deGFP-expressing HEK293 were pretreated with nystatin at a concentration of 100 μg/mL for 1 h at 37° C., followed by an incubation of 40 nM NPSC/siRNA complex. For the cellular uptake mechanism study, HeLa cells were incubated with NPSC/Cy3-siRNA (40 nM of Cy3-siRNA) and FITC-Dextran (0.5 mg/mL) for 2 h, the cells were then washed with PBS and imaged under a Zeiss LSM 710 confocal microscope. To study the effect of nystatin treatment on gene silencing efficiency, deGFP-expressing HEK293 cells were incubated with NPSC/siRNA in the presence of nystatin for 4 h and cultured with fresh medium for additional 48 h before CSLM imaging studies and flow cytometry analysis.

NPSC/siRNA Delivery Silenced deGFP Expression

Stable deGFP-expressing HEK293 cells ($1 \times 10^5$ cells/well) were seeded in a 24-well plate for 24 h prior to delivery, and the cells were washed with PBS for three times before siRNA delivery. At the day of transfection, various si_deGFP or scrambled siRNA formulations were added to cells and incubated for 4 h in Opti-MEM, followed by an additional 48 h incubation with fresh culture medium. The cells were harvested and resuspended in PBS for flow cytometry analysis on FACS LSR II (BD Biosciences). Cells suspensions were analyzed under the same parameter setting, and at least 10000 events were analyzed for each sample. For CLSM imaging of deGFP knockdown, deGFP-expressing HEK293 cells ($3.0 \times 10^5$ cells) were seeded in a 35 mm glass bottom culture dish (MatTek, MA) a day before experiment. After overnight incubation, the cells were incubated with Opti-MEM containing NPSC/si_deGFP with 60 nM siRNA at 37° C. for 4 h, followed by additional 48 h incubation. The cells were washed with PBS for three times and imaged under a Zeiss LSM 710 confocal microscope.

Cytotoxicity of NPSC/siRNA Complex deGFP-expressing HEK293 cells ($1 \times 10^5$ cells/well) were seeded in a 24-well plate 24 h prior to the experiment. At the day of experiment, cells were washed by cold PBS and treated with varied concentration of NPSC and scramble siRNA complexes (prepared in a similar procedure to that of NPSC/si_deGFP complex) for 4 h, followed by an incubation of additional 48 h with fresh culture medium. For the comparison of commercial transfection reagent, Lipofectamine 2000 and same amount of siRNA was mixed according to manufactures' instruction and dosed to HeLa cells. The cell viability was measured using AlamarBlue assay (Invitrogen, Calif.).

NPSC/siPLK1 Delivery

MDA-MB-231 cells ($2.5 \times 10^4$ cells/well) were cultured in a 48-well plate for 24 h prior to the experiment. At the day of transfection, NPSC/siPLK1 complexes (prepared as mentioned above for si_deGFP complex) were diluted by Opti-MEM and incubated with the cells for 4 h, followed by an incubation of additional 48 h with fresh culture medium. For negative controls, siPLK1 was replaced with scrambled siRNA and exposed to cells at the same concentration. The cell viability was measured using AlamarBlue assay according to manufacturer's instruction.

Detection of PLK1 Expression in siPLK1 Transfected Cells

MDA-MB-231 cells ($2 \times 10^5$) were seeded in 6-well tissue culture plates and incubated at 37° C. in 5% $CO_2$ for 24 h until 80% confluence. Various siRNA formulations were added to cells as we described in the manuscript. For western blot analysis, the transfected cells were first washed once with cold PBS, and then resuspended in 150 μL freshly prepared cell lysis buffer (containing 50 mM Tris buffer, pH=8, 150 mM NaCl, 1% Triton X-100, 10% glycerol, 1.5 mM $MgCl_2$, 1 mM EGTA) supplemented with protease inhibitor cocktail. The lysates were then clarified by centrifugation for 20 min. at 4° C. The protein concentration was determined using BCA Protein Assay Kit (Pierce, Ill.). Total cell lysate protein (33 μg) was separated on 4-12% Bis-Tris PAGE gel and then transferred (at 300 mA for 45 min) to a PVDF membrane. After blocking the blot with 5% non-fat milk in phosphate buffered saline with Tween-20 (PBST, pH 7.2) for 1 h, the membrane was incubated with monoclonal antibodies against PLKI (1:500) in 2% non-fat milk PBST solution for 24 h. After incubation in 2% non-fat milk in PBST with goat anti-mouse IgG-HRP antibody (1:10 000) for 30 min, bands were visualized using the ECL system on a Syngene G-Box (Cambridge, UK).

In Vivo Gene Silencing

All animal experiments were conducted in accordance with the guidelines of Institutional Animal Care and Use Committee (IACUC) at University of Massachusetts Amherst. Female BALB/c mice at least 6 weeks of age, received lateral tail vein injections of PBS (negative control), or NPSC containing either non-targeting siRNA (NPSC/si_SCr), or anti-GAPDH siRNA (NPSC/si_GADPH), or anti-TNF-α siRNA (NPSC/si_TNF-α) diluted in PBS at a volume of 0.01 ml g-1. The sequence of the si_GADPH and si TNF-α, provided by SIGMA-ALDRICH, INC. was: sense: 5'-CAAGAGAGGCCCUAUC-CCA[dT][dT]-3' (SEQ ID NO:4); antisense: 5'-UGGGAUAGGGCCUCUCUUG[dT][dT]-3' (SEQ ID NO:5); and sense: 5'-GUCUCAGCCUCUUCUCAUUC-CUGct-3' (SEQ ID NO:6); antisense: 5'-AGCAG-GAAUGAGAAGAGGCUGAGACAU-3' (SEQ ID NO:7), respectively.

For GADPH knockdown study, BALB/c mice were i.v. injected twice with NPSC/siRNA complexes at a siRNA dose of 0.14 $mgkg^{-1}$ at 2 days interval, blood and organs were collected and harvested 3 days post final injection. Blood was centrifuged in serum separator tubes at 5,000 r.p.m. for 10 min before TNF-α analysis by ELISA, and serum total bilirubin, alkaline phosphatase, aspartate aminotransferase, and alanine aminotransferase evaluation using commercial kits (Teco Diagnostics, Anaheim, Calif.). Each organ was cut into two parts. One half was used for ICP-MS analysis to determine total gold amount, and the other half for RT-PCR analysis of GAPDH mRNA. For TNF-α knockdown study, BALB/c mice were i.v. injected twice with NPSC/siRNA complexes at a siRNA dose of 0.28 mgkg-1 at 6 hours interval, followed by LPS (5 mg/kg, i.p.) 24 hours later. Serum TNF-α was measured by ELISA 1.5 hours after administration of LPS.

Regarding ICP-MS sample preparation, each organ was digested overnight using a 3:1 (v/v) mixture of $HNO_3$ (68%) and $H_2O_2$ (30%). On the next day, ~0.5 mL of fresh aqua regia was added, and then the sample was diluted to 10 mL with de-ionized water. A series of standard solutions (gold concentration: 20, 10, 5, 2, 1, 0.5, 0.2, 0 ppb) was prepared.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A nanoparticle-stabilized nanocapsule, consisting of:
a nanodroplet comprising an amphiphilic fluid, wherein the amphiphilic fluid is a compound having the structure of $(C_5-C_{50})$hydrocarbyl-COOH, wherein the $(C_5-C_{50})$hydrocarbyl is substituted or unsubstituted;
a plurality of nanoparticles deposed on a surface of the nanodroplet, each nanoparticle consisting of
a quantum dot comprising one or more of gold, iron oxide, cobalt ferrite, and silica, and
a ligand consisting of a $(C_0-C_{20})$hydrocarbyl group and a guanidine; and
one or more nucleic acid materials selected from the group consisting of DNA and RNA complexed to at least some of the nanoparticles,
wherein the nanoparticle-stabilized nanocapsule has a largest dimension of about 50 nm to about 1 μm.

2. The nanoparticle-stabilized nanocapsule of claim 1, wherein the nanoparticle-stabilized nanocapsule comprises about 2 to about 100,000 of the nanoparticles.

3. The nanoparticle-stabilized nanocapsule of claim 2, wherein the ligand is tethered to the quantum dot via a linker that comprises at least one of a $(C_1-C_{20})$alkylene and a poly$((C_2-C_3)$alkoxy).

4. The nanoparticle-stabilized nanocapsule of claim 3, wherein the nucleic acid material is selected from mRNA (messenger RNA), rRNA (ribosomal RNA), 7SL RNA or SRP RNA (signal recognition particle RNA), tRNA (transfer RNA), tmRNA (transfer-messenger RNA), snRNA (small nuclear RNA), snoRNA (small nucleolar RNA), SmY (SmY RNA), scaRNA (small Cajal body-specific RNA), gRNA (guide RNA), RNase P (ribonuclease P), RNase MRP (ribonuclease MRP), Y RNA, TERC (telomerase RNA component), SL RNA (spliced leader RNA), aRNA or asRNA (antisense RNA), cis-NAT (cis-natural antisense transcript), crRNA (CRISPR RNA), lncRNA (long noncoding RNA), miRNA (microRNA), piRNA (piwi-interacting RNA), siRNA (small interfering RNA), tasiRNA (trans-acting siRNA), rasiRNA (repeat associated siRNA), and 7SK (7SK RNA).

5. The nanoparticle-stabilized nanocapsule of claim 3, wherein the nucleic acid material is siRNA (small interfering RNA).

6. The nanoparticle-stabilized nanocapsule of claim 3, wherein the amphiphilic fluid is about 90 wt % to about 100 wt % of the nanodroplet.

7. The nanoparticle-stabilized nanocapsule of claim 6, wherein the $(C_5-C_{50})$hydrocarbyl is unsubstituted.

8. The nanoparticle-stabilized nanocapsule of claim 6, wherein the amphiphilic compound has the structure:

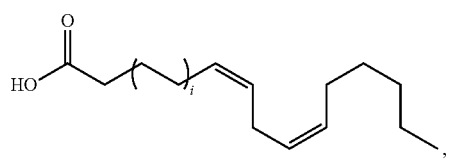

wherein i is an integer from about 1 to about 1,000.

9. A nanoparticle-stabilized nanocapsule, consisting of:
a nanodroplet comprising an amphiphilic fluid, wherein the amphiphilic fluid is a compound having the structure of $(C_5-C_{50})$hydrocarbyl-COOH, wherein the $(C_5-C_{50})$hydrocarbyl is substituted or unsubstituted;

a plurality of nanoparticles deposed on a surface of the nanodroplet, each nanoparticle consisting of
a quantum dot comprising one or more of gold, iron oxide, cobalt ferrite, and silica, and
a ligand having the structure:

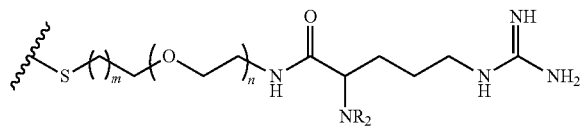

or a salt thereof, wherein each R is independently H or an alkyl group, m is an integer from about 0 to about 1,000, and n is an integer about 0 to about 1,000; and
one or more nucleic acid materials selected from the group consisting of DNA and RNA complexed to at least some of the nanoparticles, wherein the nanoparticle-stabilized nanocapsule has a largest dimension of about 50 nm to about 1 μm.

10. The nanoparticle-stabilized nanocapsule of claim 9, wherein the nanoparticle-stabilized nanocapsule comprises about 2 to about 100,000 of the nanoparticles.

11. The nanoparticle-stabilized nanocapsule of claim 9, wherein the nucleic acid material is selected from mRNA (messenger RNA), rRNA (ribosomal RNA), 7SL RNA or SRP RNA (signal recognition particle RNA), tRNA (transfer RNA), tmRNA (transfer-messenger RNA), snRNA (small nuclear RNA), snoRNA (small nucleolar RNA), SmY (SmY RNA), scaRNA (small Cajal body-specific RNA), gRNA (guide RNA), RNase P (ribonuclease P), RNase MRP (ribonuclease MRP), Y RNA, TERC (telomerase RNA component), SL RNA (spliced leader RNA), aRNA or asRNA (antisense RNA), cis-NAT (cis-natural antisense transcript), crRNA (CRISPR RNA), lncRNA (long noncoding RNA), miRNA (microRNA), piRNA (piwi-interacting RNA), siRNA (small interfering RNA), tasiRNA (trans-acting siRNA), rasiRNA (repeat associated siRNA), and 7SK (7SK RNA).

12. The nanoparticle-stabilized nanocapsule of claim 11, wherein the nucleic acid material is siRNA (small interfering RNA).

13. The nanoparticle-stabilized nanocapsule of claim 9, wherein the amphiphilic fluid is about 90 wt % to about 100 wt % of the nanodroplet.

14. The nanoparticle-stabilized nanocapsule of claim 13, wherein the amphiphilic compound has the structure:

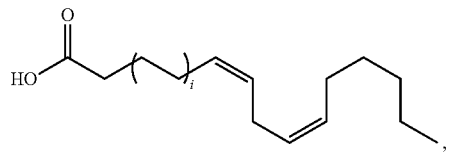

wherein i is an integer from about 1 to about 1,000.

15. The nanoparticle-stabilized nanocapsule of claim 9, wherein each R is an alkyl group.

16. The nanoparticle-stabilized nanocapsule of claim 5, wherein the amphiphilic fluid is about 100 wt % of the nanodroplet.

17. The nanoparticle-stabilized nanocapsule of claim 12, wherein the amphiphilic fluid is about 100 wt % of the nanodroplet.

* * * * *

UNITED STATES PATENT AND TRADEMARK OFFICE
CERTIFICATE OF CORRECTION

PATENT NO.         : 10,786,527 B2
APPLICATION NO.    : 15/073689
DATED              : September 29, 2020
INVENTOR(S)        : Vincent M. Rotello, Ying Jiang and Rui Tang Page 1 of 1

It is certified that error appears in the above-identified patent and that said Letters Patent is hereby corrected as shown below:

In the Specification

In Column 1, Lines 21-24 replace the paragraph immediately after the section title:
"STATEMENT REGARDING FEDERALLY FUNDED RESEARCH OR DEVELOPMENT"
with the following new paragraph:
This invention was made with government support under Grant Nos. EB014277 and GM077173 awarded by the National Institutes of Health. The Government has certain rights in the invention.

Signed and Sealed this
Twenty-sixth Day of January, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 7

<210> SEQ ID NO 1
<211> LENGTH: 19
<212> TYPE: RNA
<213> ORGANISM: Artificial
<220> FEATURE:
<223> OTHER INFORMATION: siRNA, sense strand, si_deGFP

<400> SEQUENCE: 1
augauauaga cguuguggc                                                  19

<210> SEQ ID NO 2
<211> LENGTH: 19
<212> TYPE: RNA
<213> ORGANISM: Artificial
<220> FEATURE:
<223> OTHER INFORMATION: siRNA, sense strand, siPLK1

<400> SEQUENCE: 2
gucucaaggc cuccuaaua                                                  19

<210> SEQ ID NO 3
<211> LENGTH: 19
<212> TYPE: RNA
<213> ORGANISM: Artificial
<220> FEATURE:
<223> OTHER INFORMATION: siRNA, sense strand, scrambled

<400> SEQUENCE: 3
uucuccgaac gugucacgu                                                  19

<210> SEQ ID NO 4
<211> LENGTH: 21
<212> TYPE: DNA
<213> ORGANISM: Artificial
<220> FEATURE:
<223> OTHER INFORMATION: siRNA, sense strand, si_GADPH

<400> SEQUENCE: 4
caagagaggc ccuaucccat t                                               21
```

```
<210> SEQ ID NO 5
<211> LENGTH: 21
<212> TYPE: DNA
<213> ORGANISM: Artificial
<220> FEATURE:
<223> OTHER INFORMATION: siRNA, antisense strand, si_GADPH

<400> SEQUENCE: 5
ugggauaggg ccucucuugt t                                              21

<210> SEQ ID NO 6
<211> LENGTH: 25
<212> TYPE: DNA
<213> ORGANISM: Artificial
<220> FEATURE:
<223> OTHER INFORMATION: siRNA, sense strand, si_TNF-a

<400> SEQUENCE: 6
gucucagccu cuucucauuc cugct                                          25

<210> SEQ ID NO 7
<211> LENGTH: 27
<212> TYPE: RNA
<213> ORGANISM: Artificial
<220> FEATURE:
<223> OTHER INFORMATION: siRNA, antisense strand, si_TNF-a

<400> SEQUENCE: 7
agcaggaaug agaagaggcu gagacau                                        27
```